United States Patent
Lafferty et al.

(10) Patent No.: US 12,419,791 B2
(45) Date of Patent: Sep. 23, 2025

(54) APPARATUS AND A METHOD FOR ENTRAPPING AN ELASTOMERIC MATERIAL WITH FORM-FITTING ELASTOMERIC REGIONS

(71) Applicant: Dukane IAS, LLC, St. Charles, IL (US)

(72) Inventors: Justin Marshall Lafferty, Marshfield, WI (US); Patrick Sean McNichols, Hortonville, WI (US); Kevin Miles Lysne, Fremont, WI (US); Melissa Ann Offenstein, Kaukauna, WI (US); Michael A. Snyder, Hortonville, WI (US)

(73) Assignee: Dukane IAS, LLC, St. Charles, IL (US)

( * ) Notice: Subject to any disclaimer, the term of this patent is extended or adjusted under 35 U.S.C. 154(b) by 0 days.

(21) Appl. No.: 18/912,568

(22) Filed: Oct. 10, 2024

(65) Prior Publication Data

US 2025/0120856 A1 Apr. 17, 2025

Related U.S. Application Data

(60) Provisional application No. 63/589,436, filed on Oct. 11, 2023.

(51) Int. Cl.
*A61F 13/15* (2006.01)
(52) U.S. Cl.
CPC .............................. *A61F 13/15609* (2013.01)
(58) Field of Classification Search
None
See application file for complete search history.

(56) References Cited

U.S. PATENT DOCUMENTS 6,291,039 B1 9/2001 Combe et al.
10,213,348 B2 2/2019 Gualtieri et al.
(Continued)

FOREIGN PATENT DOCUMENTS

GB 2257652 A 1/1993

OTHER PUBLICATIONS

International Searching Authority, International Search Report and Written Opinion for International Application No. PCT/2024/050861, dated Feb. 11, 2025, 16pages.

*Primary Examiner* — Barbara J Musser
(74) *Attorney, Agent, or Firm* — ICE MILLER LLP; Justin D. Swindells

(57) ABSTRACT

An apparatus for fabricating an elasticized material having at least one elastic strand transversely positioned across the apparatus. The apparatus includes a first bonding module and a second bonding module positionable in proximity to the first bonding module. At least one of the first bonding module and the second bonding module has a face with a width dimension and a circumferential axis and is rotatable about a rotation axis in a velocity vector direction, the face having a contour pattern containing a plurality of entrapment elements arranged along a width of the contour pattern, the plurality of entrapment elements having a land and a notch constructed to receive and hold the at least one elastic strand, wherein the contour pattern is arranged at an angle of between −30° and +30° from perpendicular to the at least one elastic strand with respect to the velocity vector direction, during bonding operation, and wherein the land and notch has a longitudinal axis that is at an angle of between −30° and +30° from parallel to the at least one elastic strand with respect to the velocity vector direction.

20 Claims, 18 Drawing Sheets

(56) References Cited

U.S. PATENT DOCUMENTS

| | | |
|---|---|---|
| 10,259,165 B2 | 4/2019 | Ehlert et al. |
| 10,479,025 B2 | 11/2019 | Ehlert et al. |
| 10,889,066 B2 | 1/2021 | Begrow et al. |
| 11,173,072 B2 | 11/2021 | Fritz |
| 11,191,676 B2 | 12/2021 | Koshijima et al. |
| 11,254,062 B2 | 2/2022 | Ehlert et al. |
| 11,254,066 B2 | 2/2022 | Begrow et al. |
| 11,399,989 B2 | 8/2022 | Polidori et al. |
| 11,433,620 B2 | 9/2022 | Ehlert et al. |
| 11,691,347 B2 | 7/2023 | Ehlert et al. |
| 2019/0231606 A1 | 8/2019 | Andrews et al. |
| 2020/0206040 A1* | 7/2020 | Andrews ........... A61F 13/15593 |
| 2020/0299883 A1 | 9/2020 | Begrow et al. |
| 2021/0069025 A1 | 3/2021 | Fritz |
| 2021/0205152 A1 | 7/2021 | Polidori |
| 2022/0071809 A1 | 3/2022 | Fritz |
| 2022/0250331 A1 | 8/2022 | Weiler et al. |
| 2022/0355551 A1 | 11/2022 | Ehlert et al. |
| 2023/0101562 A1 | 3/2023 | Veldman et al. |

* cited by examiner

APPARATUS AND A METHOD FOR ENTRAPPING AN ELASTOMERIC MATERIAL WITH FORM-FITTING ELASTOMERIC REGIONS

CROSS REFERENCE TO PRIOR APPLICATION

This application claims priority to, and the benefit thereof, provisional U.S. Patent application Ser. No. 63/589,436, filed on Oct. 11, 2023, the entirety of which is hereby incorporated herein by reference as if fully set forth herein.

FIELD OF THE INVENTION

The present invention relates generally to elastic nonwoven materials and, more particularly, to an apparatus and a method for making an elastic nonwoven material with form-fitting elastomeric regions.

BACKGROUND OF THE INVENTION

Elastic nonwoven materials are used in a variety of articles, including personal care articles and medical garments, among other things. The personal care articles can include, for example, adult briefs, baby diapers, adult and child pull-on pants, wearable hygiene products, and contour fit wearable products. The medical garments can include, for example, face masks, hair caps, gowns, and footwear. The articles include elastic strands that contract to gather areas of nonwoven fabric such that the nonwoven fabric functions with an elastic property to, for example, contour to the shape of the wearer.

The elastic strands are typically fabricated into the nonwoven materials using one of two principal methodologies, namely: adhesively bonding elastic strands between layers of nonwoven fabric; or entrapping tensioned elastic strands within the nonwoven fabric using ultrasonic energy. The latter methodology provides certain functional and commercial advantages compared to the former. For instance, the ultrasonic-based methodology typically eliminates certain functional deficiencies of adhesively bonded materials, such as, for example, adhesive bleed-through, stiffening, and creep that are common in adhesively bonded materials. However, even though typically requiring a complex adhesive delivery system and costly adhesive materials associated with adhesive bonding processes, in certain circumstances, and for certain applications or articles of manufacture, the adhesive-based methodology can be preferred.

U.S. Pat. No. 10,259,165 to Thomas David Ehlert, et al. and entitled "Apparatus for Fabricating an Elastic Nonwoven Material," which is hereby incorporated herein in its entirety, discloses an example of a state-of-the-art rotary ultrasonic bonding system and method. Referring to FIG. 1, the patent describes a system 100 that includes a supply station 102, a processing station 104, and a collection station 106. The system 100 is arranged to directly entrap multiple tensioned elastic strands 120, 124, 128, 132 from respective supply spools 118, 122, 126, 130, within nonwoven fabrics 112, 116 from respective supply spools 110, 114 using a rotary ultrasonic apparatus 200 included in the processing station 104, without the use of any adhesive. In this regard, the apparatus has an anvil module and a horn module that cooperate to perform the bonding operation by guiding the elastic strands via notches on an anvil face and applying ultrasonic energy to the nonwoven fabrics 112, 116 and tensioned elastic strands 120, 124, 128, 132 via a horn located in close proximity to the anvil. The collection station 106 collects the resultant elastic nonwoven material 134 on to a puller roller 136.

Other examples of state-of-the-art bonding systems and methods include those described in Patent Nos. U.S. Pat. No. 6,291,039 to Robert Combe et al., U.S. Pat. No. 10,213,348 to Diego Gualtieri et al., U.S. Pat. No. 10,479,025 to Thomas David Ehlert et al., U.S. Pat. No. 10,889,066 to Brandon Leo Begrow, et al., U.S. Pat. No. 11,173,072 to Jeffrey W. Fritz, U.S. Pat. No. 11,191,676 to Miwa Koshijima et al., U.S. Pat. No. 11,254,062 to Thomas David Ehlert et al. U.S. Pat. No. 11,254,066 to Brandon Leo Begrow et al., U.S. Pat. No. 11,399,989 to Domenico Polidori et al., U.S. Pat. No. 11,433,620 to Thomas David Ehlert et al., and U.S. Pat. No. 11,691,347 to Thomas David Ehlert et al., and those described in Patent Application Publication Nos. US 2019/0231606 to Robert Earl Andrews et al., US 2021/0205152 to Domenico Polidori, US 2022/0071809 to Jeffrey W. Fritz, US 2022/0250331 to Dave Weiler et al., US 2022/0355551 to Thomas David Ehlert et al., and US 2023/0101562 to Cory D. Veldman et al. All of the foregoing patents and published patent applications are hereby incorporated herein by reference.

State-of-the-art ultrasonic energy-based and adhesive-based methodologies provide significant benefits related to making elastic nonwoven materials. The inventors have discovered significant improvements to those methodologies for making an elastic nonwoven material with form-fitting elastomeric regions.

SUMMARY OF THE INVENTION

According to an aspect of the disclosure, an apparatus is provided for fabricating an elasticized material having at least one elastic strand transversely positioned across the apparatus, the apparatus comprising: a first bonding module; and a second bonding module positionable in proximity to the first bonding module, wherein at least one of the first bonding module and the second bonding module has a face with a width dimension and a circumferential axis and is rotatable about a rotation axis in a velocity vector direction, the face having a contour pattern containing a plurality of entrapment elements arranged along a width of the contour pattern, the plurality of entrapment elements having a land and a notch constructed to receive and hold the at least one elastic strand, wherein the contour pattern is arranged at an angle of between −30° and +30° from perpendicular to the at least one elastic strand with respect to the velocity vector direction, during bonding operation, and wherein the land and notch has a longitudinal axis that is at an angle of between −30° and +30° from parallel to the at least one elastic strand with respect to the velocity vector direction.

In an embodiment of the apparatus, another of the at least one of the first bonding module and the second bonding module includes an adhesive applicator.

In an embodiment of the apparatus, another of the at least one of the first bonding module and the second bonding module includes an ultrasonic welding device containing a horn.

In an embodiment of the apparatus, the notch has a groove width and the land has a seal width, wherein each of the plurality of entrapment elements has a land-to-notch ratio of about 60:40, or less.

In an embodiment of the apparatus, the land width is between 0.005 inches and 0.013 inches; and/or the notch has a depth that is between 0.004 inches and 0.015 inches.

In an embodiment of the apparatus, the notch has a width that is between 0.005 inches and 0.013 inches.

In an embodiment of the apparatus, the one of the plurality of elastic strands is between 320 and 1,100 decitex.

In an embodiment of the apparatus, the land has a machine direction land length that is between 0.015 inches and 0.060 inches.

In an embodiment of the apparatus, the notch has a machine direction notch length that is between 0.015 inches and 0.060 inches.

In an embodiment of the apparatus, the contour pattern has a machine direction spacing of 0.10 inches, or greater.

In an embodiment, the apparatus comprises a strand applicator, wherein the strand applicator is configured to transversely position the at least one elastic strand in one of the plurality of entrapment elements in alignment with the contour pattern.

In an embodiment, the apparatus comprises an applicator, wherein the applicator has a strand application end arranged to position and lay at least one elastic strand in the plurality of notches in alignment with the contour pattern, and wherein the strand application end is located 100 mm, or less, from the contact line between the first bonding module and second bonding module.

In an embodiment, the apparatus comprises an applicator having a strand application end located at a lag distance from the contact line between the first bonding module and second bonding module and configured to position and lay at least one elastic strand in one of the plurality of notches in alignment with the contour pattern, wherein the applicator moves the at least one elastic strand according to a profile which includes kingpin effect corrections created by the lag distance.

In an embodiment of the apparatus, the cam profile having the kingpin effect corrections is configured to move the at least one elastic strand transversely across a width of the second bonding module in alignment with the strand applicator end to-and-fro across the width dimension according to the contour pattern, and each of the plurality of elastic strands in the plurality of entrapment elements in alignment with the curved shape of the ridge line. The applicator king pin lag distance can determine the minimum radius being created.

In an embodiment of the apparatus, the minimum radius at any point on the contour pattern is 30% less than the king pin lag distance.

According to another aspect of the disclosure, a system is provided for fabricating a elasticized material having at least one elastic strand transversely positioned across the apparatus, the system comprising: a supply station; and a processing station that includes a first bonding module and a second bonding module positionable in proximity to the first bonding module, wherein at least one of the first bonding module and the second bonding module has a face with a width dimension and a circumferential axis and is rotatable about a rotation axis in a velocity vector direction, the face having a ridge line containing a plurality of entrapment elements arranged along a width of the ridge line, each of the plurality of entrapment elements having a ridge and a notch constructed to receive and hold a respective one of the plurality of elastic strands, wherein the ridge line has a curved shape arranged to guide the plurality of elastic strands during a bonding operation, and wherein the notch has a longitudinal notch axis that is perpendicular to said one of the plurality of elastic strands, and the longitudinal notch axis is formed at an angle between −30° and +30° with respect to the velocity vector direction.

In an embodiment, the system further comprises: an applicator arm having a strand application end located at a lag distance from another of said at least one of the first bonding module and the second bonding; a controller configured to drive the applicator arm according to a cam profile to position and lay each of the plurality of elastic strands in the plurality of entrapment elements in alignment with curved shape of the ridge line, wherein the cam profile includes kingpin effect corrections to correct for a kingpin effect created by the lag distance.

According to another aspect of the disclosure, a method is provided for fabricating an elasticized material having a curved elastic section containing a plurality of entrapped elastic strands, the method comprising: positioning a first bonding module in proximity to a second bonding module, wherein: at least one of the first bonding module and the second bonding module has a face with a width dimension and a circumferential axis and is rotatable about a rotation axis in a velocity vector direction, the face having a ridge line containing a plurality of entrapment elements arranged along a width of the ridge line, each of the plurality of entrapment elements having a ridge and a notch constructed to receive and hold a respective one of the plurality of elastic strands; the ridge line has a curved shape arranged to guide the plurality of elastic strands during a bonding operation; and the notch has a longitudinal notch axis that is perpendicular to said one of the plurality of elastic strands, and the longitudinal notch axis is formed at an angle between −30° and +30° with respect to the velocity vector direction; and directing, by a strand applicator arm, each of the plurality of elastic strands to the plurality of entrapment elements along the curved shape of the ridge line.

In the method, directing each of the plurality of elastic strands to the plurality of entrapment elements along the curved shape of the ridge line can comprise feeding each of the plurality of elastic strands from a supply station in an oscillatory manner along the width dimension of the face.

In the method, directing each of the plurality of elastic strands to the plurality of entrapment elements along the curved shape of the ridge line can comprise directing each of the plurality of elastic strands into respective ones of the plurality of entrapment elements.

In the method, another of the at least one of the first bonding module and the second bonding module can include an adhesive applicator.

In the method, another of the at least one of the first bonding module and the second bonding module can include an ultrasonic welding device containing a horn.

In the method, the notch has a width and the land has a seal width, wherein each of the plurality of entrapment elements can have a land-to-notch ratio of about 60:40, or less.

In the method, the notch-to-land ratio can be about 53:47, or less.

In the method, the notch width can be about 0.009 inches, or greater, and the seal width can be about 0.007 inches, or greater.

In the method, the one of the plurality of elastic strands can be between 680 and 1,000 decitex.

The method can further comprise positioning a strand application end of the strand applicator arm at a lag distance from another of the at least one of the first bonding module and the second bonding module, operating the strand applicator arm according to a cam profile that includes kingpin effect corrections to correct for a kingpin effect created by the lag distance.

According to a further aspect of the disclosure, a nonwoven material having a curved elastic section containing a plurality of entrapped elastic strands can be made by the apparatus, system, or method above.

Additional features, advantages, and embodiments of the disclosure may be set forth or apparent from consideration of the detailed description and drawings. Moreover, it is to be understood that the foregoing summary of the disclosure and the following detailed description and drawings provide nonlimiting examples that are intended to provide further explanation without limiting the scope of the disclosure as claimed.

BRIEF DESCRIPTION OF THE DRAWINGS

The accompanying drawings, which are included to provide a further understanding of the invention, are incorporated in and constitute a part of this specification, illustrate embodiments of the invention and together with the detailed description serve to explain the principles of the invention.

Figure 1:
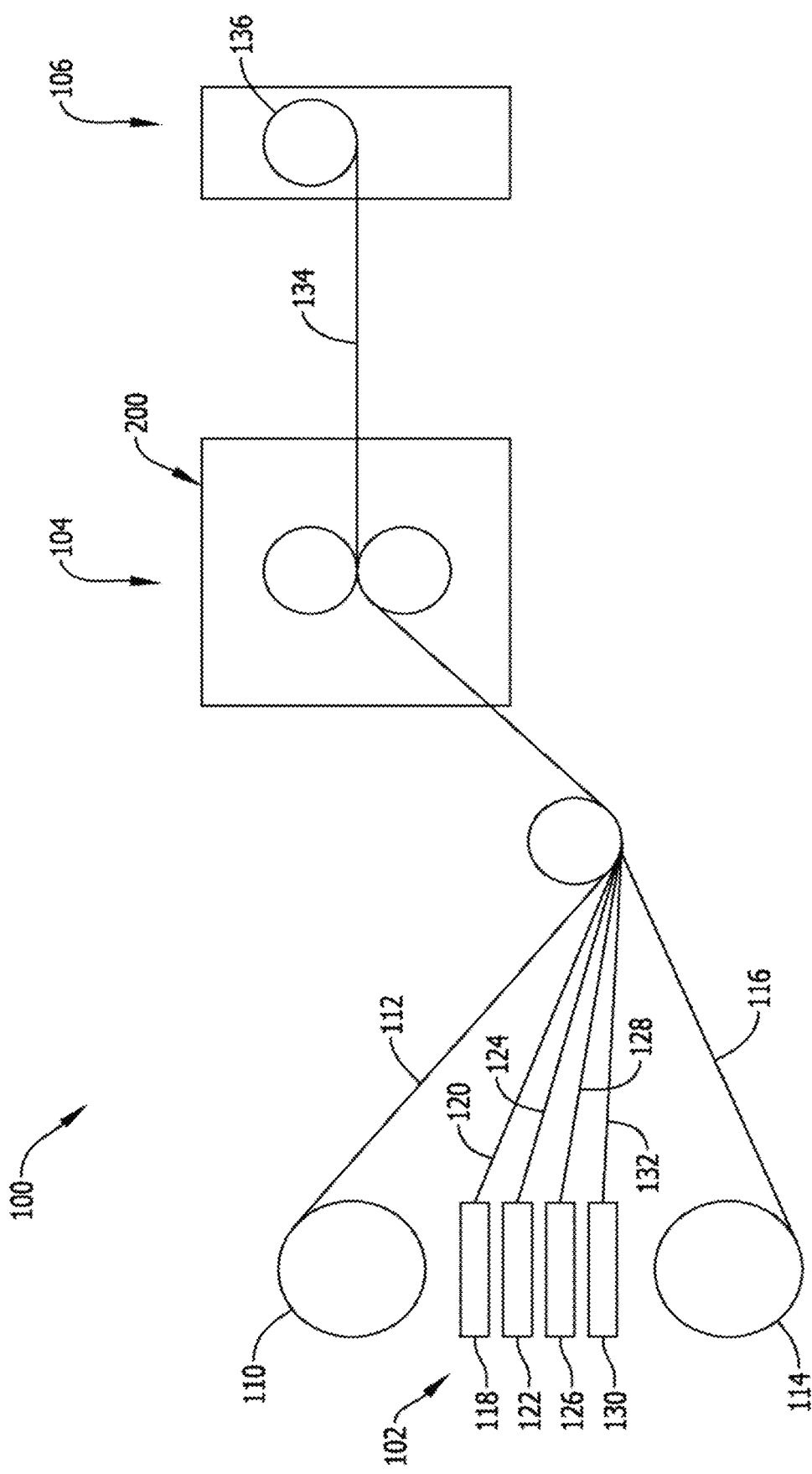
FIG. 1 illustrates a nonlimiting example of a state-of-the-art bonding system and methodology that uses ultrasonic energy to entrap tensioned elastic strands within nonwoven fabrics.

The present disclosure is further described in the detailed description that follows.

DETAILED DESCRIPTION OF THE INVENTION

The invention and its various features and advantageous details are explained more fully with reference to the non-limiting embodiments and examples that are described or illustrated in the accompanying drawings and detailed in the following description. It is noted that features illustrated in the drawings are not necessarily drawn to scale, and features of one embodiment can be employed with other embodiments, as those skilled in the art will recognize, even if not explicitly stated. Descriptions of well-known components and processing techniques may have been omitted so as to not unnecessarily obscure the embodiments of the invention. The examples are intended merely to facilitate an understanding of ways in which the invention can be practiced, and to further enable those skilled in the art to practice the embodiments of the invention. Accordingly, the examples and embodiments should not be construed as limiting the scope of the invention. Moreover, it is noted that like reference numerals represent similar parts throughout the several views of the drawings.

Figure 2:
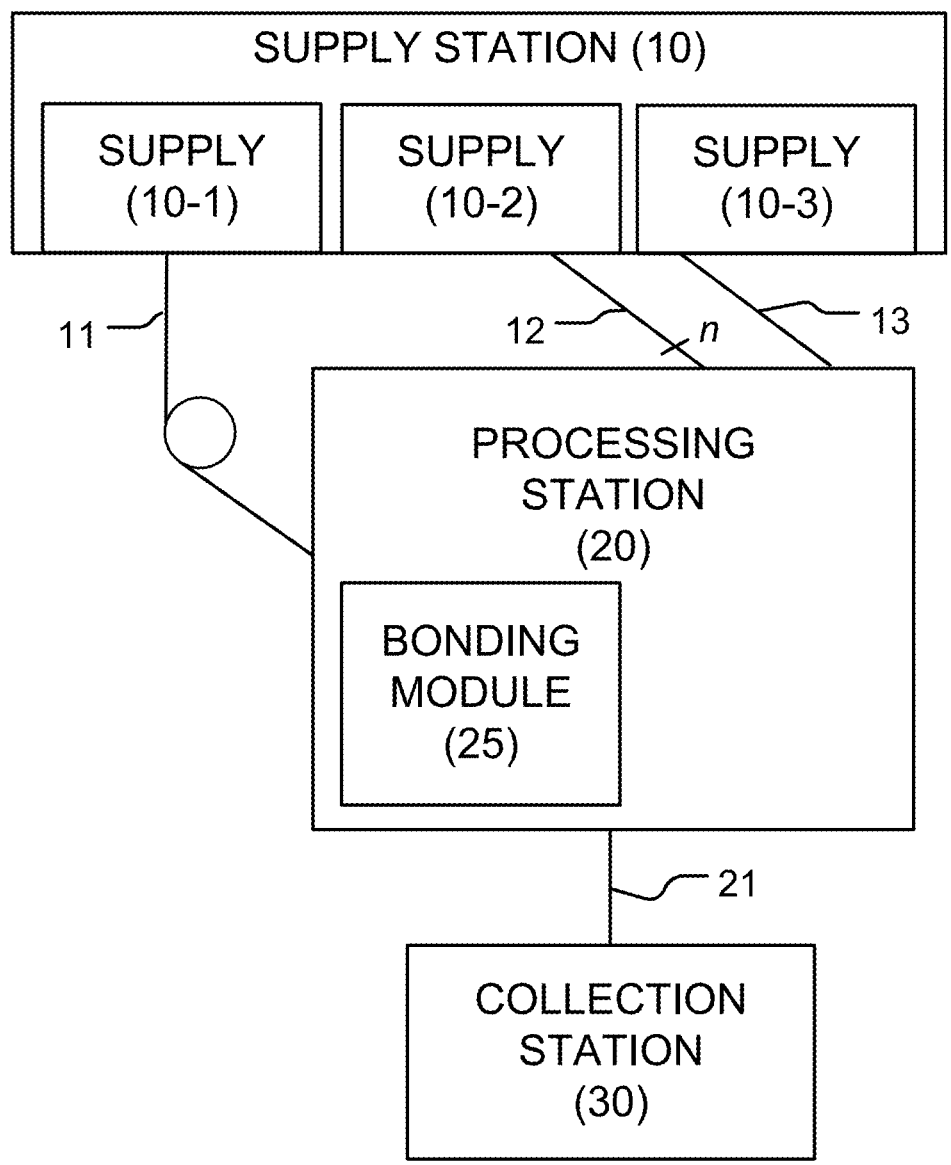
FIG. 2 illustrates a nonlimiting embodiment of a system for fabricating an elastic nonwoven material with contoured or form-fitting elastomeric regions.

Referring to the drawings, FIG. 2 illustrates a system 1 for fabricating an elastic nonwoven material with contoured or form-fitting elastomeric regions. The illustrated system 1 includes a supply station indicated generally by 10, a processing station indicated generally by 20, and a collection station indicated generally by 30. The supply station 10 includes a plurality of supply substations 10-1, 10-2, 10-3, each of which includes one or more rolls of material. The processing station 20 includes at least one bonding module 25.

The supply substations 10-1 and 10-3 each include a roll containing a material 11 and 13, respectively. In various embodiments, the materials 11, 13 include nonwoven fabrics, spunlace, films, and other substrate materials that can be bonded using ultrasonic welding. The materials 11 and 13 can be of the same type of material, or a different type or material. The supply substations 10-1, 10-3 can include additional rolls containing materials. In an embodiment, the supply substations 10-1 and 10-3 include the rolls 110 and 114 seen in FIG. 1. The materials 11, 13 are supplied to the processing station 20. The materials 11, 13 can be tensioned and supplied in tensioned form to the processing station 20.

The supply substation 10-2 includes n supply spools (where n is a positive integer greater than 0) each containing an elastic strand 12. The n elastic strands 12 are tensioned and supplied substantially in parallel or at different angles and, using one or more rollers, redirected and supplied substantially in parallel in tensioned form to the processing station 20. In an embodiment, the supply substation 10-2 includes the supply spools 120, 122, 126, 130 shown in FIG. 1.

Figure 14:
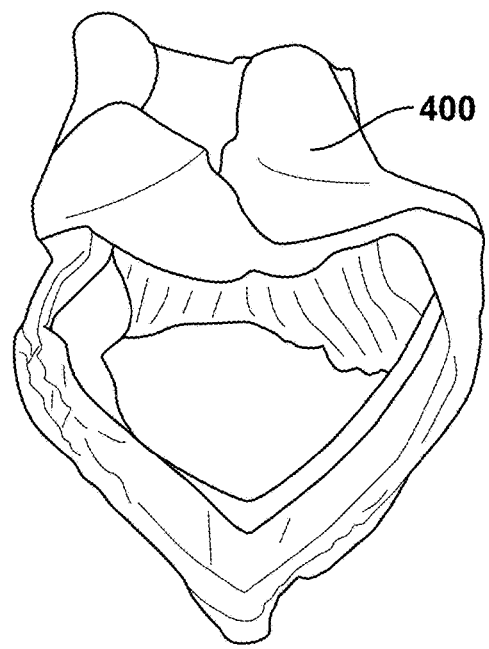
FIG. 14 illustrates an example of an article of manufacture.

The processing station 20 is arranged to receive the materials 11, 13 and the tensioned n elastic strands 12 and directly entrap the n strands 12 within the materials 11, 13 using a rotary bonding apparatus 200 included in the processing station 20 and output a bonded material 21 contoured to match the die cut profile (not shown) used to remove excess material and create articles of manufacture (for example, the article 400 shown in FIG. 14). In this regard, the apparatus 200 has the at least one bonding module 25 to perform a bonding operation by guiding the n elastic strands 12 via respective entrapment elements (for example, 210EL shown in FIG. 9) and applying either (1) an adhesive by an adhesive applicator in an embodiment (for example, the adhesive applicator 260, shown in FIG. 5) to predetermined, discrete, minimal-dimensioned spots on each strand 12 and material 13 or (2) ultrasonic energy to the materials 11, 13 having the n elastic strands 12 tensioned and entrapped therebetween using at least one of the horn and anvil in another embodiment (for example, the horn 220H and the anvil 210, shown in FIGS. 3-4). The collection station 106 collects the bonded material 21 on to a puller roller. In an embodiment, the collection station 106 includes the puller roller 136 shown in FIG. 1.

Figure 3:
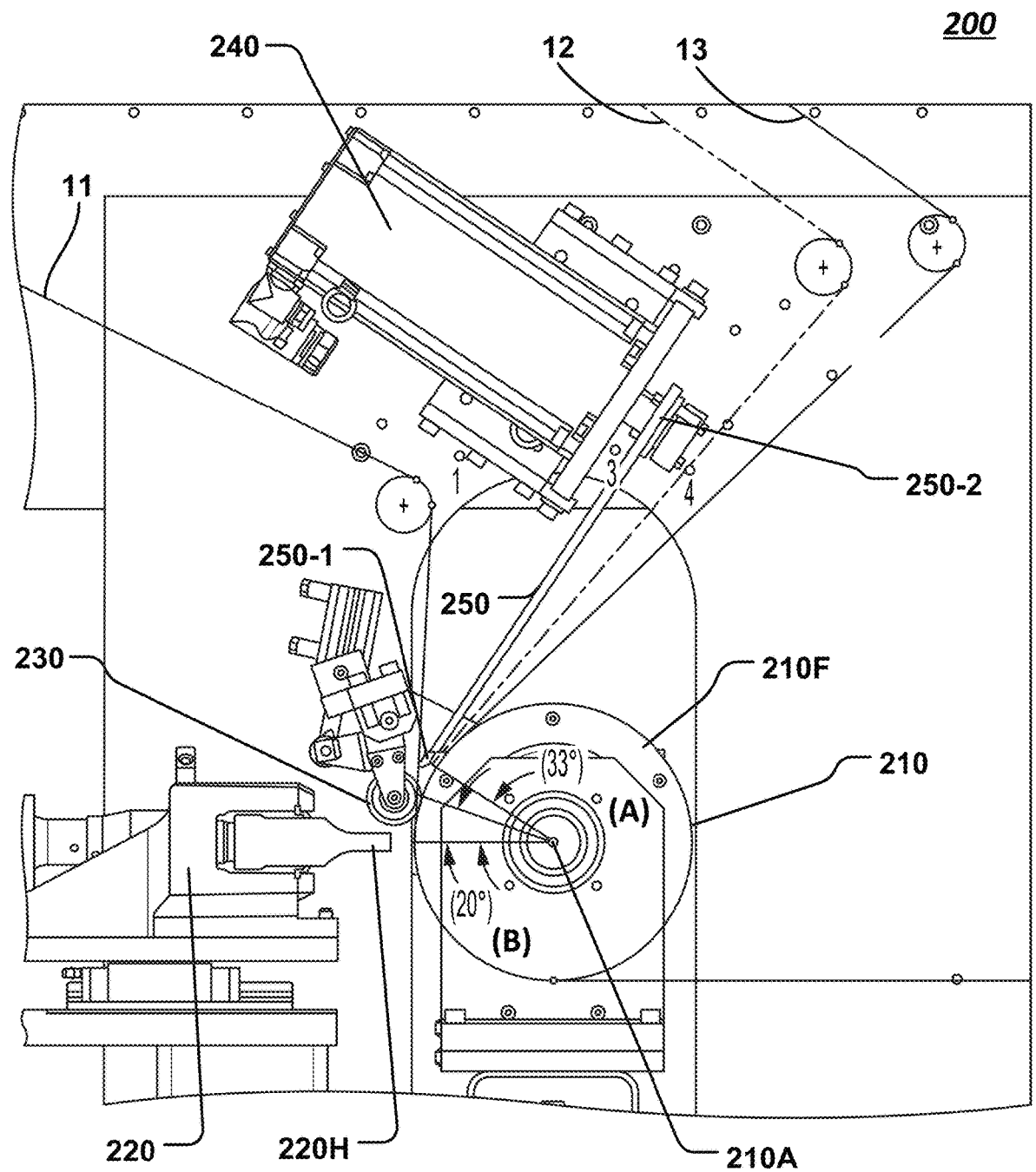
FIG. 3 illustrates an embodiment of the rotary bonding apparatus.
Figure 4:
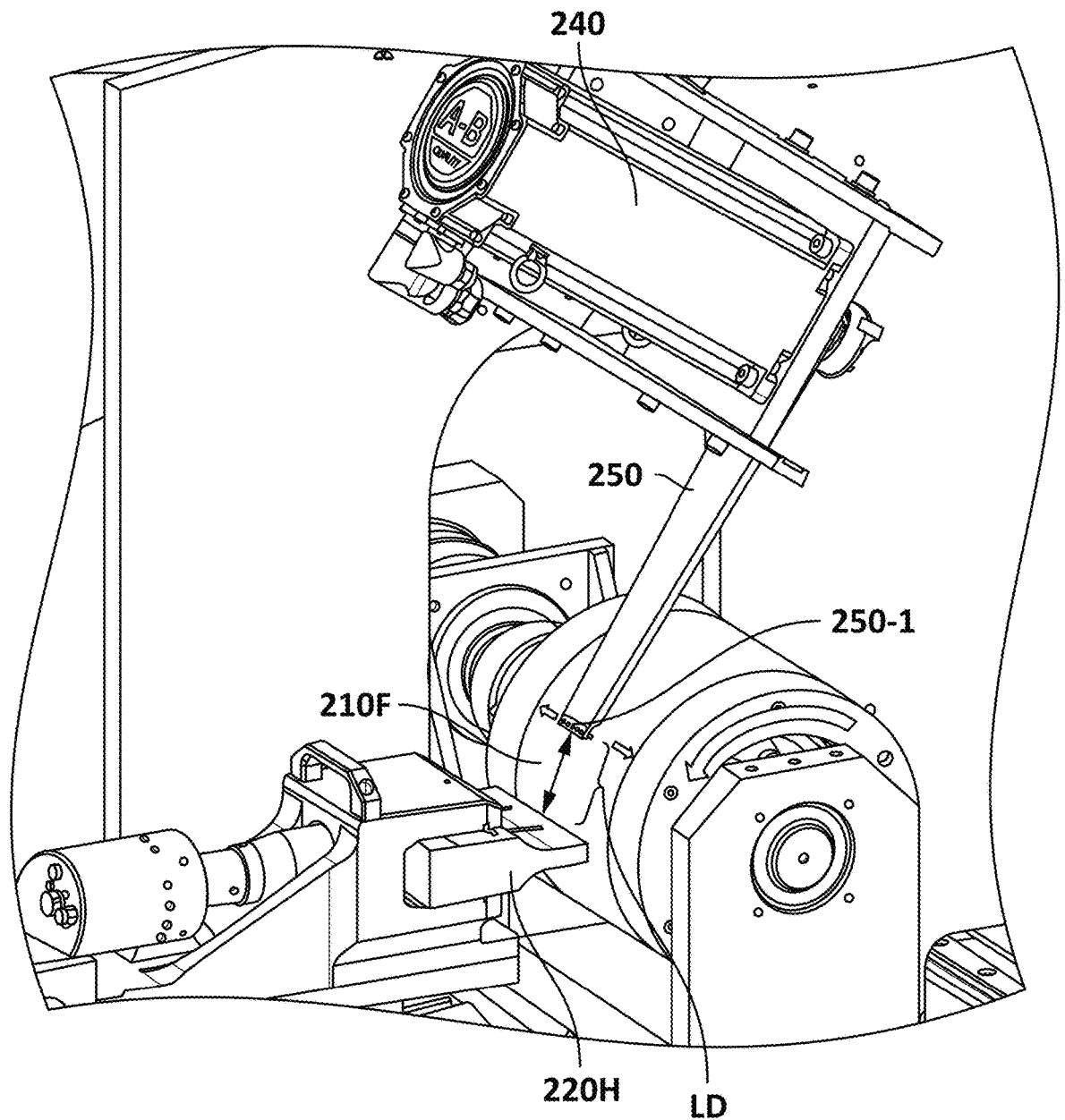
FIG. 4 illustrates a perspective view of the rotary bonding apparatus in FIG. 3.

In variations of the embodiment depicted in FIGS. 3-4, the at least one module 25 includes either or both a first bonding module and a second bonding module. In various embodiments, the at least one module 25 includes both the first bonding module and the second bonding module. In at least one embodiment, the first bonding module and the second bonding module include the anvil module and the horn module, respectively, set forth in commonly owned U.S. Pat. No. 10,259,165.

In at least one embodiment, the first bonding module and the second bonding module include the anvil 210 and the horn 220H, respectively, provisioned with entrapment elements to receive and hold the n strands 12 to match a curve profile of an article of manufacture (for example, the article 400, shown in FIG. 14). The second bonding module can include an ultrasonic welding device that includes the horn 220H.

Figure 5:
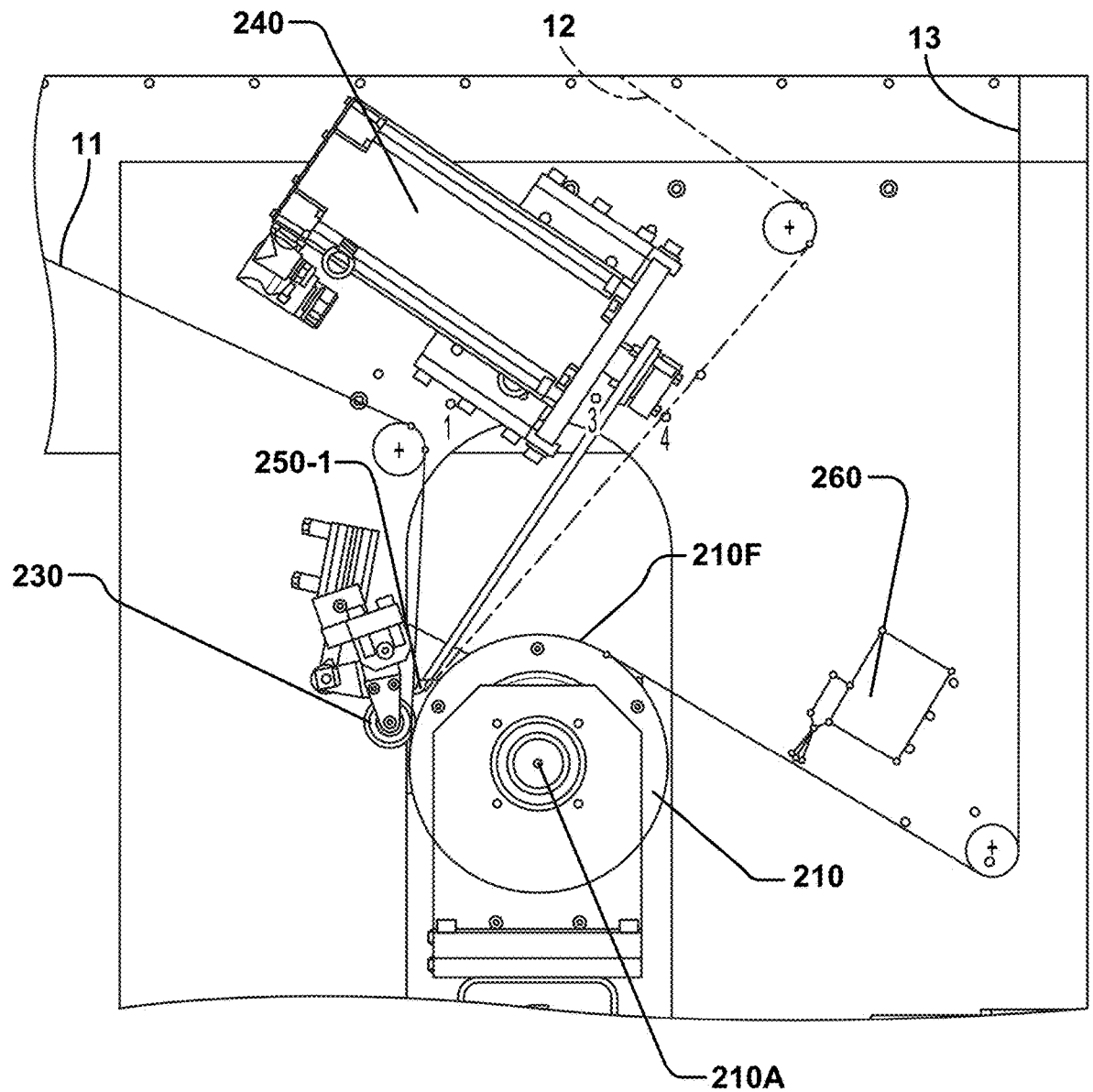
FIG. 5 illustrates another embodiment of a rotary bonding apparatus.

In the embodiment depicted in FIG. 5, the at least one module 25 includes the applicator 260 and a snapback roll 230 that is configured to apply pressure to the layers of materials 11, 13 and the entrapped n strands 12 therebetween, pressing and securing each of the n strands 12 into respective entrapment elements on the anvil 210 to match a curve profile of the article of manufacture.

Figure 10:
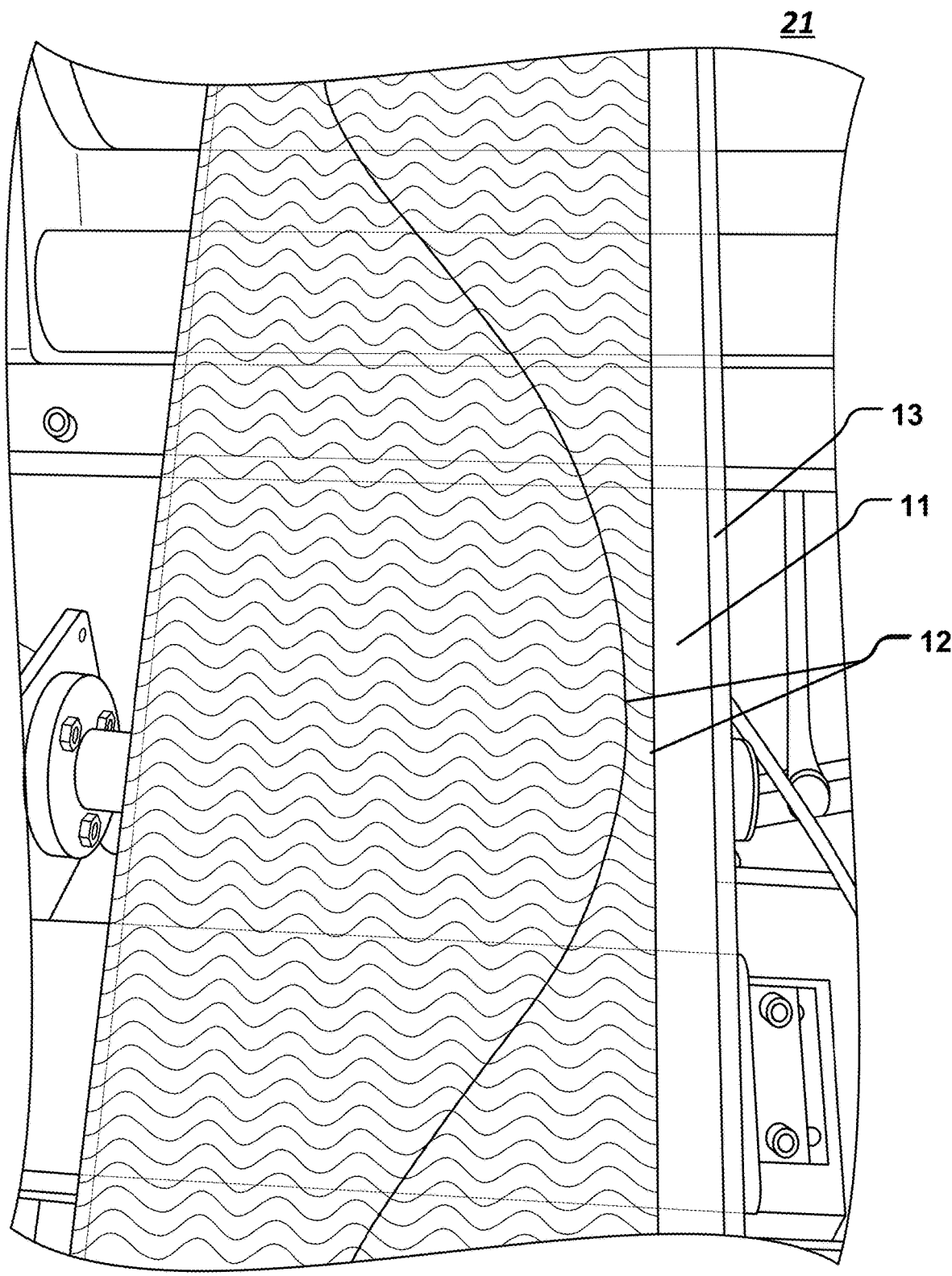
FIG. 10 illustrates an example of a bonded material output by the apparatus of FIGS. 3-4.

FIG. 3 illustrates an embodiment of the rotary bonding apparatus 200 that can be included in the processing station 20 and arranged to receive the materials 11, 13 and the tensioned n elastic strands 12 and directly entrap the n strands 12 within the materials 11, 13, without the use of any adhesive, and output the bonded material 21 contoured to match curve profile of the article of manufacture—for example, the curve profile of the article seen in FIGS. 10 and 14. In an embodiment, the n strands 12 are positioned and entrapped in the material layers 11, 13 to match a die-cut profile used to remove excess material and create the article of manufacture (for example, the article 400 shown in FIG. 14). In this regard, the apparatus 200 has the anvil 210 and the ultrasonic welding device 220 containing a horn 220H which cooperate to perform the bonding operation by positioning and holding the n elastic strands 12 via entrapment elements provided on either or both a surface of the horn 220H and a surface of the anvil 210—that is, an anvil face 210F—and applying ultrasonic energy to the materials 11, 13 and tensioned n elastic strands 12 to bond the layers 11, 13 to each other with the tensioned strands 12 trapped therebetween. The collection station 106 collects the bonded material 21 on to a puller roller. In an embodiment, the collection station 106 includes the puller roller 136 shown in FIG. 1.

Referring to FIG. 3, in addition to the anvil 210 and the ultrasonic welding device 220, the apparatus 200 includes at least one elastic snapback roll 230, a motor (or mechanical driver) 240, and an elastic strand applicator arm 250. The elastic strand applicator arm 250 is positioned to be as close to the horn 220H as possible to minimize a lag distance LD (shown in FIG. 4) between the horn 220H and the applicator arm 250 that creates a kingpin effect. At the same time, the applicator arm 250 is positioned with respect to the horn 220H and the anvil face 210F such that an angle A between a line from, and perpendicular to, a rotational axis 210A of the anvil 210 to a tangent point 250-1 at an end of the application arm 250 and a line from, and perpendicular to, the rotational axis 210A to a central axis of the horn 220H position is approximately thirty-three degrees (33°), or less.

In some embodiments, the horn 220H and the anvil face 210F are positioned at an angles A greater than 33°. In such embodiments, the apparatus 200 includes at least one additional snapback roll 230 positioned between the applicator arm 250 and the horn 220H to facilitate positioning and holding the n strands 12 in predetermined entrapment elements on the anvil face 210F as the anvil 210 rotates through a bonding cycle. The bonding cycle can include a section of the bonded material 21 required for manufacture of a single unit of article of manufacture.

FIG. 4 is a perspective view of the rotary ultrasonic bonding apparatus 200 that provides a detailed view of the applicator arm 250 as it oscillates to-and-fro across a width of the anvil surface 210F (the cross-machine direction). As seen in the drawing, even though a tangent point on a strand application end 250-1 of the applicator arm 250 is positioned to be as close as possible to the horn 220H, operational requirements of the horn 220H, snapback roll 230, and the applicator arm 250 necessitate providing the lag distance LD between the horn 220H and the strand applicator end 250-1 of the arm 250. The lag distance LD introduces a kingpin effect that is addressed by the apparatus 200 according to a cam profile.

The strand application end 250-1 of the applicator arm 250 includes discrete guides for each of the n elastic strands 12. The n guides each include a low friction guide device such as an eyelet made of metal or other durable material.

In some embodiments, the horn 220H and applicator arm 250 can be positioned such that the LD is between 0 mm and 90 mm, with a maximum lag distance LD being 90 mm. In various embodiments, the lag distance LD is set to approximately 40 mm, 52 mm, and 65 mm. Other lag distances LD are contemplated.

In some embodiments, the lag distance LD is greater than 90 mm, in which case the apparatus 200 includes the at least one additional snapback roll 230 positioned between the end 250-1 of the arm 250 and the horn 220H to facilitate holding the n strands 12 in the predetermined entrapment elements on the anvil face 210F in which the strands 12 are laid by the applicator arm 250, as the anvil 210 rotates through the bonding cycle.

In at least one embodiment, the apparatus 200 is configured such that the material layer 13 wraps around at least three hundred and five degrees (305°) of the anvil face 210F, with respect to the rotational axis of the anvil 210. In embodiments having less than a 305° wrap-around area on the anvil face 210F, the apparatus 200 includes the at least one additional snapback roll 230 to facilitate holding the material layer 13 in place and the n strands 12 in their respective predetermined entrapment elements on the anvil face 210F.

In the embodiment depicted in FIGS. 3-4, the motor 240 includes a phase-locked-loop (PLC) controlled servo motor to drive the applicator arm 250 and oscillate the arm end 250-1 with respect to the anvil face 210F during operation. In this regard, the applicator arm 250 is attached at its distal end 250-2 to the motor 240, with the strand application end 250-1 positioned to be as close as possible to the horn 220H. The applicator arm 250 is driven by the motor 240 such that the applicator end 250-1 moves to-and-fro along a width of the anvil face 210F according to a cam profile for the particular anvil face 210F as it positions and lays each of the tensioned n elastic strands 12 into entrapment elements 210EL (shown in FIGS. 7-9) on the anvil face 210F to match a curve profile of the article of manufacture as the anvil 210 rotates. In an embodiment, the motor 240 is controlled and driven by a controller 300 (shown in FIG. 13).

In the apparatus 200, the applicator arm 250, driven by the motor 240, performs a synchronous cam motion according to the cam profile, moving the tensioned n elastic strands 12 to match a curve profile of the article, such as, for example, a curve profile of a die cutout design for the article.

In an embodiment, the apparatus 200 can include a mechanical driver in place of (or in addition to) the motor 240. The mechanical driver can be configured to move the applicator arm 250 to perform a synchronous cam motion according to the cam profile, moving the tensioned n elastic strands 12 to match a curve profile of the article, such as, for example, a curve profile of a die cutout design for the article.

The snapback roll 230 is arranged to limit the snap-back potential of the tensioned n elastic strands 12 that become severed between the anvil 210 and the horn 220H of the welding device 220, and prevent any of the broken strands 12 from snapping back to the supply substation 10-2. The snapback roll 230 is configured to apply pressure to the layers of material 11, 13 with the strands 12 therebetween, forcing any strand 12 into a notch 210N that is not in a notch when the strand 12 (with layers 11, 13) comes into contact with the snapback roll 230 to prevent the strand from breaking during the ultrasonic welding operation. The snapback roll 230 serves at least two functions, including securing all n strands 12 in respective notches 210N and limiting the snap-back potential of any of the n strands 12 that become severed between horn 220H and the anvil 210 during a bonding operation. The snapback roll 230 effectively prevents any strand 12 from breaking and, should a strand 12 break, it catches the broken strand 12 between the roller and the anvil 210, thereby preventing the broken strand 12 from snapping back to its respective supply spool in the supply substation 10-2.

In an embodiment, the snapback roll 230 rotates by virtue of being in contact with anvil 210 and any broken elastic strand 12 that is caught at the interface of the snapback roll 230 and the anvil 210 is automatically fed back into the interface between the horn 220H and the anvil 210. As such, the snapback roll 230 serves as a self-threading device for any broken elastic strand 12.

The snapback roll 230 can be positioned to be as close as possible to the position of the horn 220H to minimize spunbond wrap on the snapback roll 230. In an embodiment, the snapback roll 230 is positioned at an angle B (with respect to the rotational axis 210A) of approximately twenty degrees (20°) or less from the position of the horn 220H. As noted above, in some embodiments the apparatus 200 includes a plurality of snapback rolls 230 positioned in series along the anvil face 210F in between the applicator end 250-1 and the horn 220H.

To facilitate minimizing the occurrence of any strand 12 being cut between the horn 220H and the anvil 210 during a bonding operation, it is desirable to effectively hold the tensioned n elastic strands 12 in place within respective predetermined notches 210N (shown in FIG. 9) on the anvil face 210F while the layers of material 11, 13 are bonded together between the horn 220H and the anvil 210. In this regard, one or more operational parameters in the system 1 can be controlled to minimize the occurrence of any elastic strand 12 being cut during a bonding operation. In an embodiment, operational parameters of the apparatus 200 are controlled to minimize cutting of any elastic strand 12, including: the amplitude of vibration of the horn 220H; the pressure at which the horn 220H contacts the anvil face 210F; the geometry and location of each entrapment element 210EL on the anvil face 210F; the decitex and tension force of each of the n elastic strands 12; and the basis weight of the materials 11, 13. In an embodiment, the operational parameters are supplied by the controller 300 (shown in FIG. 13).

Figure 11:
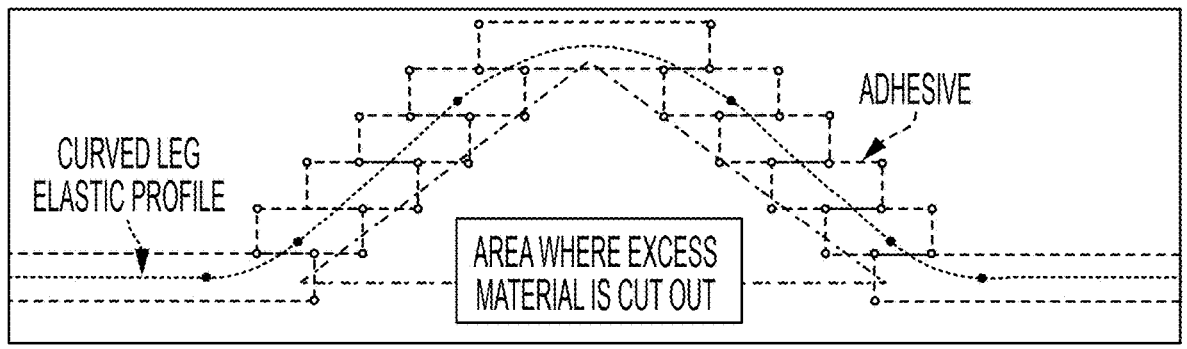
FIG. 11 illustrates an example of adhesive application in the apparatus in FIG. 5.

FIG. 5 illustrates an embodiment of an adhesive-based rotary bonding apparatus, which can be included in the processing station 20 (shown in FIG. 2). In the embodiment depicted in FIG. 5, the apparatus includes the same components as the apparatus 200 (including having a plurality of snapback rolls 230), except that the ultrasonic welding device 230 is omitted and an adhesive applicator 260 is included. In the apparatus depicted in FIG. 5, the applicator arm 250 performs a synchronous cam motion moving n elastic strands 12 to match a die cutout product design. Referring to the diagram in FIG. 11, the adhesive applicator 260 applies an adhesive in an intermittent pattern with multiple adhesive nozzles (not shown) placed side by side along the width of the anvil face 210F (for example, in the cross-apparatus direction) and timed to operate and eject adhesive onto the layer 13 in discrete, minimal-dimensioned spots on the layer 13 to match the product design strand profile. Each discrete spot is sized to the minimum dimensions required to bond the layers 11, 13 with the tensioned n strands 12 entrapped therebetween, immovably with respect to the layers 11, 13. The minimum dimensions of each spot minimize the amount of adhesive used, thereby reducing cost and other disadvantages typical of adhesive bonding processes. The snapback roll 230 compresses the top facing material layer 11, the curved n elastic strands 12, the discrete, minimal-dimensioned spots of adhesive, and the bottom facing material layer 13 together, creating a bonded material 21 having elastic strands 12 curved to match to the curve profile of the die cut used to remove excess material.

Figure 6:
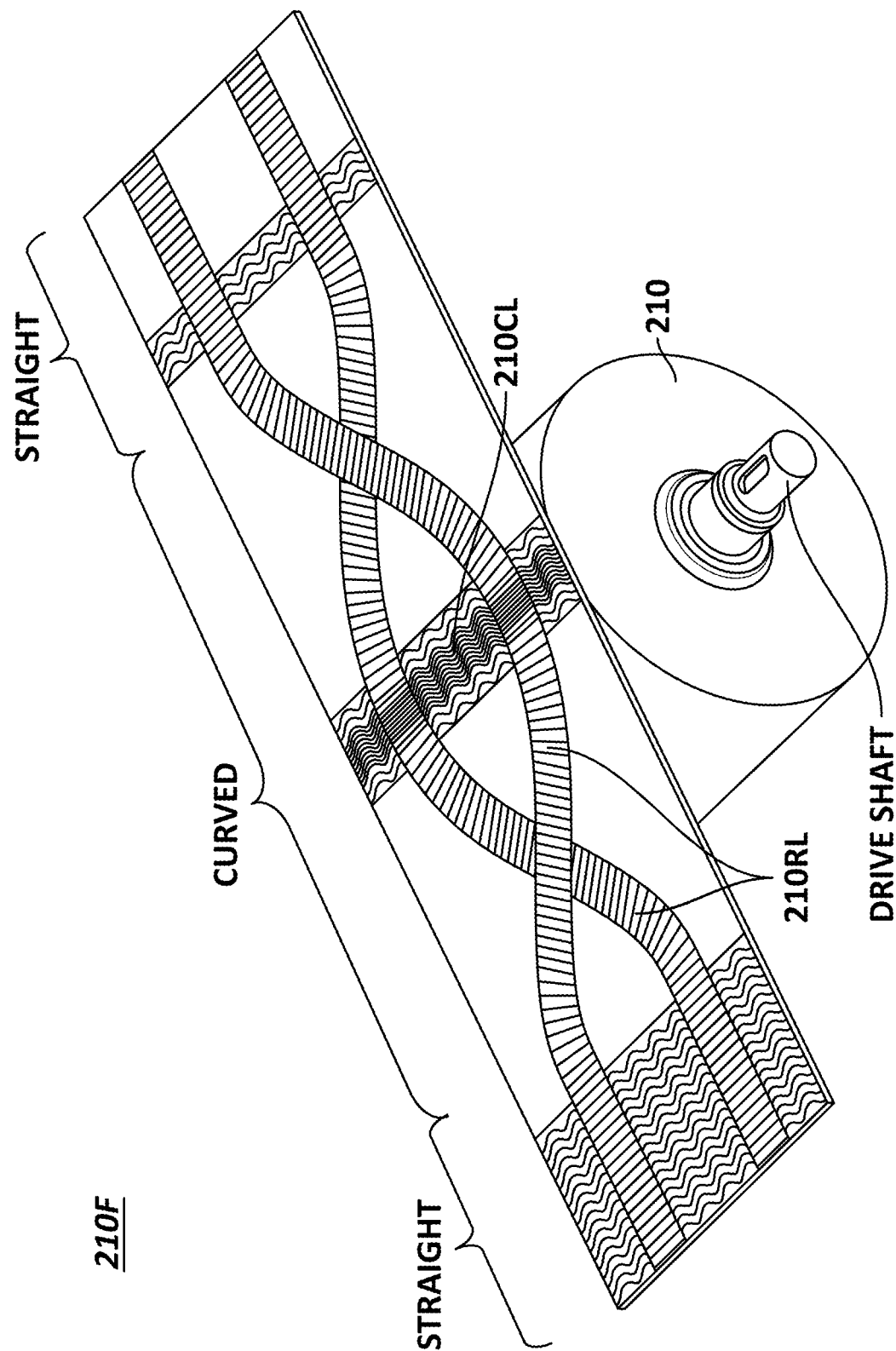
FIG. 6 illustrates a laid-flat depiction of an embodiment of a geometry of an anvil face.

FIG. 6 depicts a laid-flat illustration of an embodiment of a geometry of the anvil face 210F. In some embodiments, the anvil face 210F is installed on or affixed to a portion or the entirety of the surface of the anvil 210, and in other embodiments the anvil face 210F is part of the anvil 210 formed during fabrication of the anvil 210. The anvil face 210F forms the outer surface of the anvil 210 that includes the entrapment elements 210LE (shown in FIG. 9) that hold and guide the n elastic strands 12 during a bonding operation. The anvil face 210F has a width dimension oriented parallel to the anvil rotational axis 210A (shown in FIG. 3), a length dimension that, being the outer surface of the anvil 210, is the circumference of the anvil 210, and the rotational axis 210A. As seen in the drawing, the anvil face 210F includes at least one ridge line 210 RL that is shaped to match the curve profile of the elastic in the article of manufacture (for example, article 400 shown in FIG. 14). The anvil face 210F can include a cut line 210Cl that aligns with a knife cut operation (not shown) to cut the bonded material 21 into sections of material to be used in assembling the article, which in the example shown in FIG. 14 is two sections that can be attached to form the shape seen in FIG. 14. The ridge line 210RL includes a plurality of rows (or columns) of entrapment elements 210EL (shown in FIG. 9), each of which is dimensioned and located to secure and hold an elastic strand 12 at a predetermined location on the anvil face 210F to match the corresponding location for that strand in the article profile, including the curved elastic region of the article profile. The ridge line 210RL, including the rows (or columns) of entrapment elements 210EL and cut line 210CL, in the aggregate, form an anvil pattern AP on the anvil face 210F. The rows (or columns) of entrapment elements 210EL can be constructed as a plurality of discrete lines positioned adjacent each other much like the track ballasts that support railroad tracks, each line having a plurality of entrapment elements 120EL located along the width of the ridge line 210RL, and, in at least one embodiment, defining the width of the ridge line 210RL. The apparatus 200 can be provided with a unique anvil pattern AP for each unique of article of manufacture.

In an alternative embodiment, the ridge line 210RL can include a plurality of entrapment elements 210EL, each of which includes a single notch 210N and land 210R that extends as a single notch and land along the entire length of the ridge line 210RL.

In FIG. 6, the anvil pattern AP includes a pair of ridge lines 210RL for illustrative purposes. In an embodiment, the anvil pattern AP has only a single ridge line 210RL having a curved section (for example, sinusoidal shape) and a straight section. The radius of the curved section of the ridge line 210RL can be set to 20 mm (or R20 mm) or larger, such as 50 mm (R50 mm), 75 mm (R75 mm), 100 mm (R100 mm), or larger. In some embodiments, the straight section makes up fifty percent (50%) or less of the ridge line 210RL, such that the ratio of straight section to curved section is 1:1 or less. The ridge lines 210RL are configured to be continuous and provide continuous contact for a bonding pattern. The ridgeline 210R can have any curve shape suitable to a particular article of manufacture.

Figure 7:
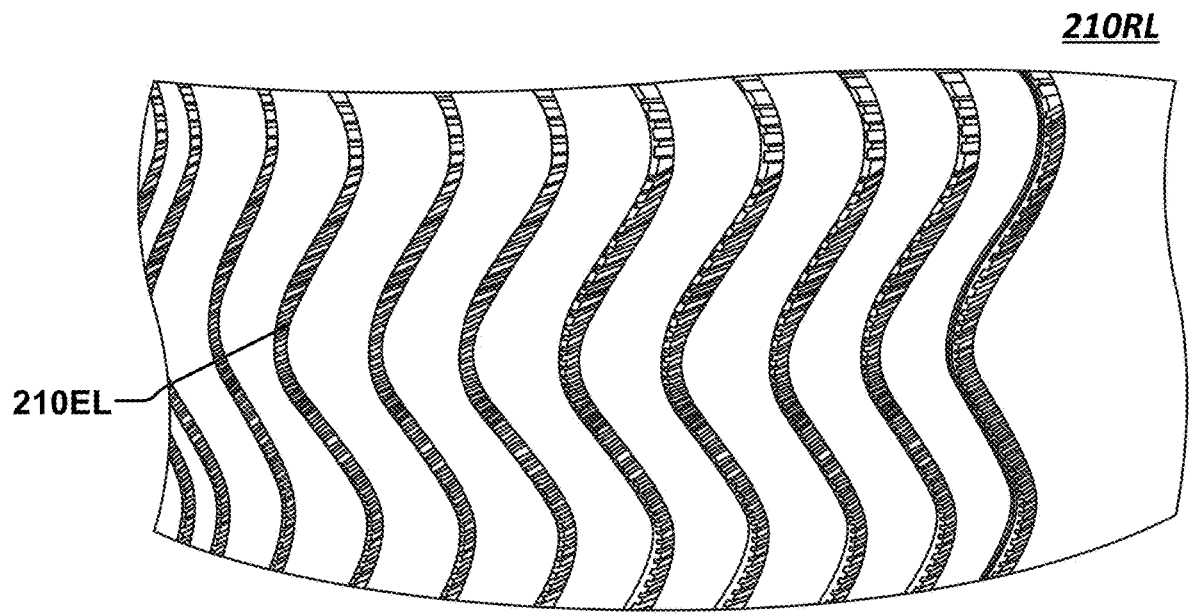
FIG. 7 illustrates a partial view of an embodiment of the anvil pattern that includes a plurality of non-linear ridge lines.

FIG. 7 illustrates a partial view of an embodiment of the anvil pattern AP that includes a ridge line 210RL having a plurality of rows 210REL of entrapment elements 210EL. The entrapment elements 210EL are arranged to provide substantially continuous contact for a bonding pattern of the article of manufacture via the discrete rows 210REL (or columns) of engagement elements 210EL. In some embodiments, the entrapment elements 210EL are arranged to provide continuation contact for the bonding pattern, as discussed above with the extended engagement elements. In various embodiments, the engagement elements 210EL are arranged in varying shapes and dimensions to form a unique anvil pattern AP that is suited to the shape, dimensions, and material to be bonded for a particular article of manufacture. The anvil pattern AP is shaped, sized, and arranged to position and hold each of the n elastic strands 12 in a respective entrapment element 210EL and guide the elastic strand 12 with the layers 11, 13 during the bonding operation.

Figure 8:
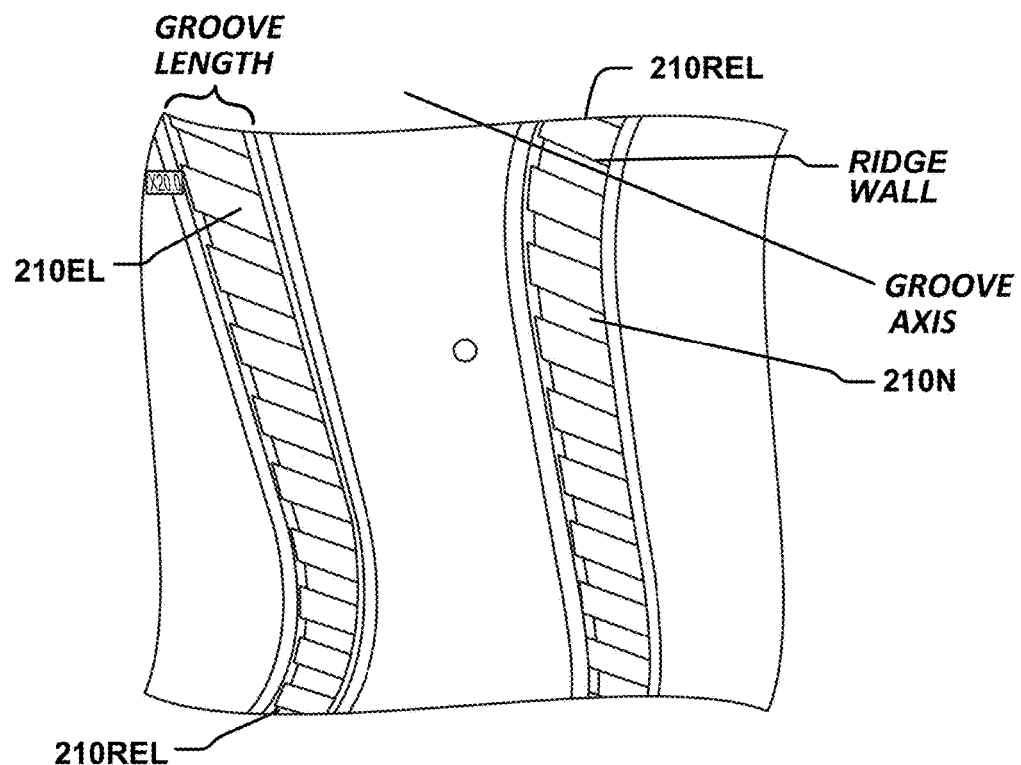
FIG. 8 illustrates a detailed view of portions of a pair of ridge lines in an embodiment of the anvil pattern.

FIG. 8 illustrates a detailed view of portions of a pair of rows 210REL in an embodiment of the anvil pattern AP. Each row 210REL contains a plurality of entrapment elements 210EL, each having of a notch 210N formed adjacent to a land 210R. Each land 210R is constructed to receive and hold the material layer 13 and each notch 210N is constructed to receive the layer 13 and a strand 12, and position and hold the strand 12 in the recess of the notch 210 with the underlying portion of the layer 13 as the anvil 210 rotates. Then, when the second material layer 11 is received, the entrapment elements 210 EL hold both layers 11, 13 and the entrapped n elastic strands 12 as the anvil 210 rotates through the bonding operation by the horn 220H.

In the adhesive-based embodiment shown in FIG. 5, which does not have the ultrasonic welding device 220, the second material layer 11 is received and held by the rows 210REL of entrapment elements 210EL together with the adhesive, the entrapped n strands 12 in respective notches 210N, and the material layer 13 as the anvil 210 rotates through the adhesion operation.

Figure 9:
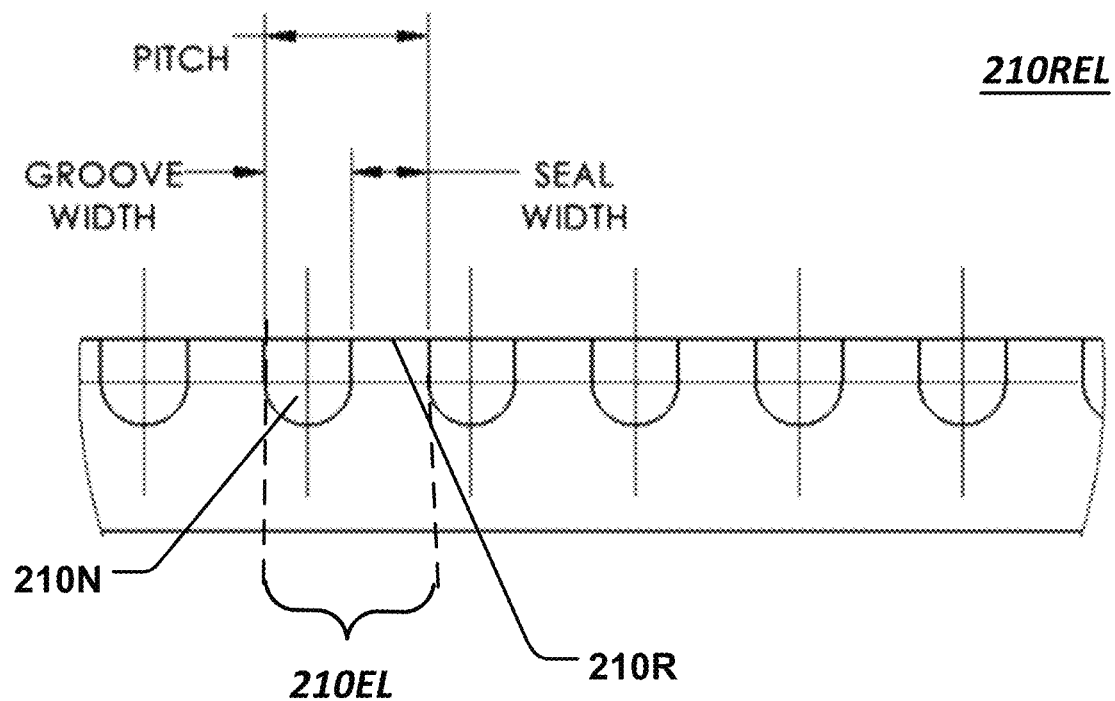
FIG. 9 illustrates a depiction of an enlarged view of a portion of a ridge line.

FIG. 9 depicts an enlarged view of a portion of the row (or column) 210REL to illustrate a plurality of entrapment elements 210EL in the row. Each entrapment element 210EL consists of the notch 210N and an adjacent land 210R arranged in a row 210REL in the ridge line 210RL on the anvil face 210F. Each notch 210N in each row 210REL in the ridge line 210RL is arranged be perpendicular (90°) at all times to the direction of the longitudinal axis of the respective strand 12 that is to be received from the applicator end 250-1 and held by that notch 210R as the anvil 210 rotates through the bonding or adhesion operations. In various embodiments, the notch 210N has a notch width (or groove width) that is between about 0.005 inches and about 0.013 inches for elastic strands 12 having a decitex in the range of 300 decitex to 1,100 decitex, a land width (or seal width) that is between about 0.013 inches and about 0.005 inches, and a pitch that is the sum of the groove width and the seal width. Each notch 210N has a longitudinal notch axis (or groove axis) that is parallel to the plane of the wall of adjacent land 210R and perpendicular to the radius of the anvil 210. The notch axis of each notch 210N in the row 210REL is constructed to have an angle that is in the range of −30° to +30° relative to the angle of the velocity vector direction of the anvil 210 when rotating. In the aggregate, the notches 210N are constructed along the length of the ridge line 210RL to provide a single continuous groove along the entire length of the ridge line 210RL for each respective one of the n elastic strands 12, contouring each elastic strand to the curved die-cut pattern for the article.

In some embodiments, each notch 210N in a row 210REL has a notch width that is about 0.009 inches, or larger, and a notch or land length that is about 0.008 inches, or smaller, for a notch-to-land (or groove-to-land) ratio of about 53:47, or greater. In another embodiment, the notch-to-land ratio is set to about 55:45, with the notch width being set to 0.009 inches and the notch or land length being about 0.007 inches. These embodiments can effectively handle elastic strands 12 that are from 1,100 decitex to 300 decitex, or from 1,000 decitex to 680 decitex.

In various embodiments, the notch-to-land ratio is set to 40:60, or greater, and preferably greater than 50:50, such as, for example, 53:47, 55:45, or greater.

FIG. 10 illustrates an example of the bonded material 21 output by the apparatus 200. As seen in the drawing, the n elastic strands 12 are shaped and entrapped in a curved shape in the material layers 11, 13 that matches the elastic curve profile of the die-cut pattern of the article 400 (shown in FIG. 14). The bonded material 21 can include at least one elastic strand that has a curved section and at least one elastic strand that has a straight section.

Referring to FIG. 4, although the elastic strand applicator arm 250 is positioned to be as close to the horn 220H as possible, any lag distance LD greater than 0 between the horn 220H and the applicator arm 250 causes a kingpin effect that, if not corrected, results in misalignment and incorrect positioning of the n elastic strands 12 in the bonded material 21. If not corrected, the misalignment of the n elastic strands 12 results in breakage of the elastic strands prior to bonding. For instance, when an elastic strand 12 is not properly aligned to fall into a predetermined notch 120N on the anvil face 210F, that elastic strand can be placed on another portion of the ridge line 120RL (or be placed entirely off the ridge line 120RL) that causes angular misalignment to the grooves that breaks the strand.

Figure 12:
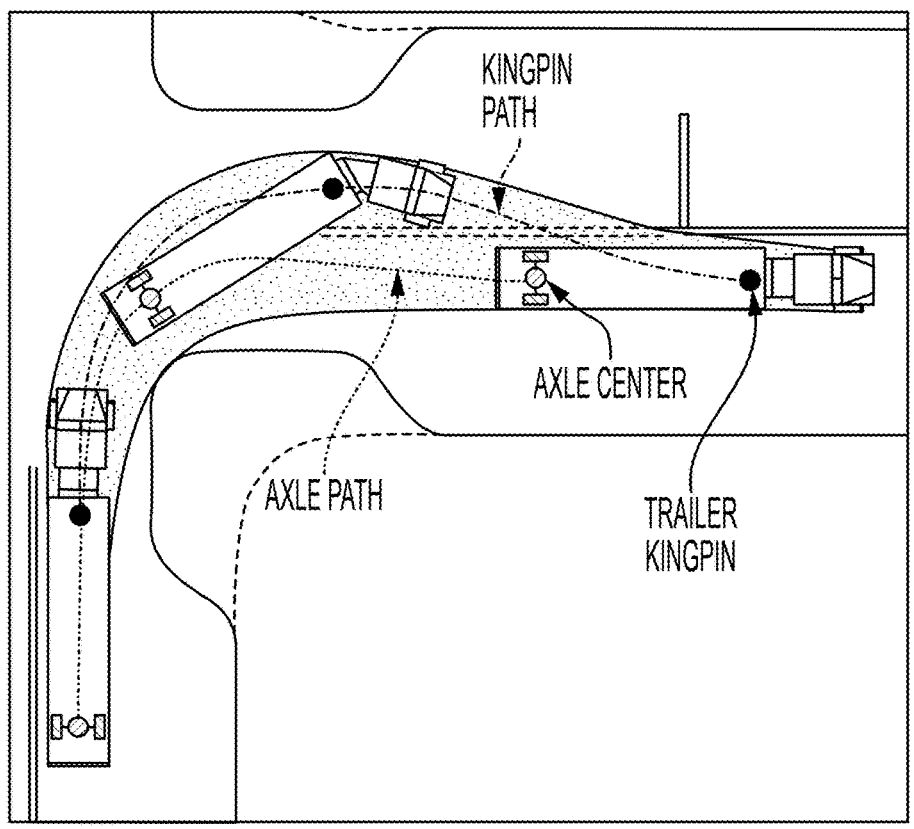
FIG. 12 illustrates an example of a kingpin effect.

Referring to FIG. 12, the kingpin effect can best be illustrated by a tractor and trailer rig taking a ninety degree (90°) turn, as seen in the drawing. When taking the turn, the rear-most trailer axle travels a shorter distance (smaller turning radius) than the trailer kingpin, which must travel a greater distance (larger turning radius) during the turn for the rear-most trailer axle to clear the corner.

Figure 13:
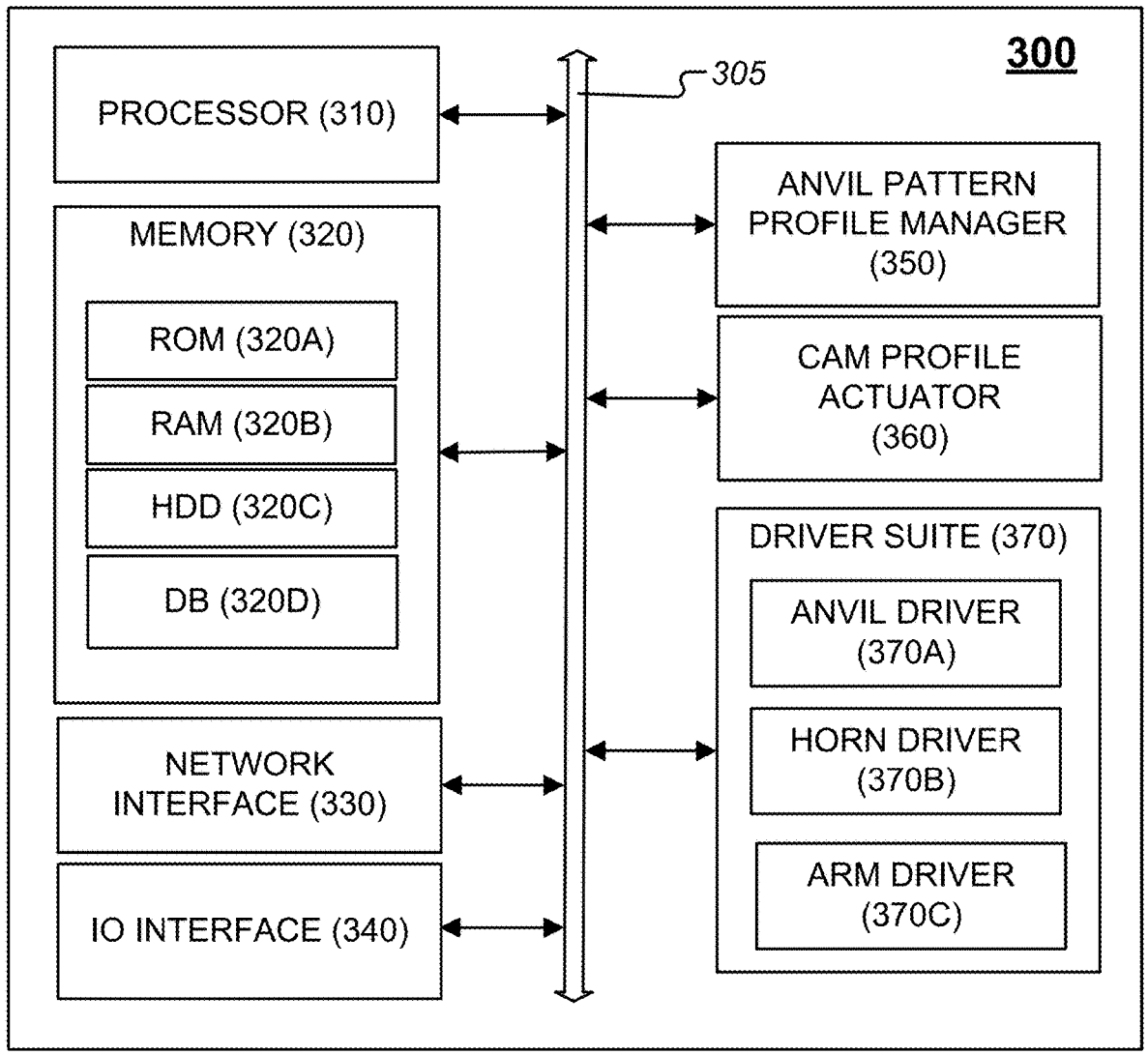
FIG. 13 illustrates a block diagram of an embodiment of a controller that can be included in the apparatus in FIGS. 3-5 or located externally and connected to the apparatus.

FIG. 13 illustrates a block diagram of an embodiment of a controller 300 that can be included in the apparatus 200, or located externally and connected through one or more wired or wireless connections to the apparatus 200. The controller 300 includes a bus 305, a processor 310, a memory 320, a network interface 330, an input-output (IO) interface 340, an anvil pattern profile manager 350, a cam profile actuator 360 and a driver suite 370. The driver suite 370 includes an anvil driver 370A, a horn driver 370B, and an arm driver 370C. Any of the components 310 to 370 can be interconnected using various buses, including the bus 305, and can be mounted on a common motherboard or in another manner, as appropriate.

The processor 310 can be arranged to process instructions for execution within the controller 300, including instructions stored in the memory 320. The processor 310 can include any of various commercially available processors. Dual microprocessors and other multi-processor architectures can be employed as the processor 310. The processor 310 can include a central processing unit (CPU), an application-specific integrated circuit (ASIC), or a graphic processing unit (GPU). The processor 310 is arranged to interact with all of the components in the controller 300 to carry out or facilitate the processes described herein.

The bus 305 can include any of several types of bus structures that can further interconnect to a memory bus (with or without a memory controller), a peripheral bus, and a local bus using any of a variety of commercially available bus architectures.

The memory 320 includes a read-only memory (ROM) 320A, a random-access memory (RAM) 320B, a hard disk drive (HDD) 320C, and a database (DB) 320D. The memory 320 can provide nonvolatile storage of data, data structures, and computer-executable instructions, and can accommodate the storage of any data in a suitable digital format. The memory 320 can include a computer-readable medium that can hold executable or interpretable computer code (or instructions) that, when executed by the processor 310, cause the steps, processes and methods in this disclosure to be carried out.

The computer-readable medium can be contained in the memory 320, and can include sections of computer code that, when executed by the processor 310, cause the controller 300 to drive the anvil 210, the ultrasonic welding device 220, and the motor 240 to align and lay the n strands 12 into respective notches 210N on the anvil face 210F as the anvil 210 is rotated and apply ultrasonic energy to the layers 11, 13 having the n strands 12 entrapped therebetween o form the bonded material 21.

In the adhesive-based embodiment of the apparatus depicted in FIG. 5, the computer-readable medium contained in the memory 320 can exclude the sections of computer code that cause the controller to drive the ultrasonic welding device 220 and, instead, include a section of computer code that, when executed by the processor 310, causes the adhesive applicator 260 to apply adhesive to predetermined areas on the material layer 13, including, for example, to operate one or more nozzles (not shown) to apply a predetermined amount of adhesive on the areas of the material layer 13.

A basic input-output system (BIOS) can be stored in the ROM 320A, which can include a non-volatile memory, an erasable programmable read-only memory (EPROM), or an electrically erasable programmable read-only memory (EEPROM). The BIOS can contain the basic routines that help to transfer instructions and data between any one or more of the components in the controller 400, such as during start-up.

The RAM 320B can include dynamic random-access memory (DRAM), a synchronous dynamic random-access memory (SDRAM), a static random-access memory (SRAM), a nonvolatile random-access memory (NVRAM), or another high-speed RAM for caching data.

The HDD 320C can include, for example, an enhanced integrated drive electronics (EIDE) drive, a serial advanced technology attachments (SATA) drive, or any suitable hard disk drive for use with big data. The HDD 320C can be configured for external use in a suitable chassis (not shown).

The DB 320D includes one or more databases, including one or more relational databases. The DB 320D includes anvil pattern AP profiles for each anvil face 210F that is usable with the apparatus 200. Each anvil pattern profile includes data such as rotational velocity (for example, in a range of 100 products-per-minute (ppm) to 400 ppm, or greater), rates of acceleration/deceleration, dimensions (width, length, height, radius, weight), electric voltage and current values, electric frequency values, pressure values, lag distance LD, and specifications for each component necessary for accurate and effective entrapment and bonding of the n elastic strands 12 within the layers 12, 13 by the apparatus 200, including the shape, location, and dimensions of the ridge line 210RL, including the location and dimensions of each entrapment element 210EL (including groove width, seal width, pitch, and notch axis angle). For the adhesive-based embodiment of the apparatus depicted in FIG. 5, the anvil pattern AP profile can include data such as the shape, location and dimension of each discrete minimal-dimensioned adhesive spot, and the amount of adhesive to be applied to the spot.

A computer program product can be tangibly embodied in a non-transitory computer-readable medium, which can be contained in the memory 320. The computer program product can contain instructions that, when executed by the processor 310, cause the processor 310 to perform one or more methods or operations, such as those included in this disclosure.

The network interface 330 can be connected via a communication link to a network (not shown), which can include the Internet. The network interface 330 can include a wired or a wireless communication network interface (not shown) or a modem (not shown). The network interface 330 can include a receiver (not shown), a transmitter (not shown) or a transceiver (not shown). The network interface 330 can be configured to communicate with a computer (not shown) located external to, and remote from the apparatus, via a network.

The input-output (IO) interface 340 can receive commands or data from an operator via a user interface (not shown), such as, for example, a keyboard (not shown), a touch-display (not shown), a mouse (not shown), a pointer (not shown), a stylus (not shown), an interactive voice response (IVR) system (not shown), a microphone (not shown), a speaker (not shown), or a display device (not shown). The received commands and data can be forwarded from the IO interface 340 as instruction to data signals, via the bus 305, to any of the components in the controller 300.

The anvil pattern profile manager 350 includes a device or computer program that is configured to retrieve applicable anvil pattern profile data for the anvil face 210F installed in the apparatus 200 from the memory 320 and provide the profile parameters to the cam profile actuator 360 or driver suite 370 to operate the anvil 210 via the anvil driver 370A, the ultrasonic welding device 220 via the horn driver 370B, and the applicator arm 250 via the arm driver 370C. To operate the anvil 210, the profile parameters include rotational velocity, rate of acceleration/deceleration, and the dimensions of the anvil 210 (for example, width, radius, weight). To operate the ultrasonic energy device 220, the profile parameters include voltage and current values, frequency value, pressure value, and time duration of energy application. To operate the application arm 250, the profile parameters include the shape, location, and dimensions of each ridge line 210RL, including the location and dimensions of each entrapment element 210EL (groove width, seal width, pitch, and notch axis angle).

The cam profile actuator 360 includes a device or computer program that is configured to calculate the kingpin effect based on profile parameters, including specification data for the anvil face 210F, including location and dimensions of each entrapment element 210EL in each row 210REL in the ridge line 210RL, and the lag distance LD (shown in FIG. 4) between the horn 220H and the tangent point on the arm end 250-1 and create a cam profile that corrects for kingpin effects and matches exactly the article design profile, including curved elastic sections, to the anvil pattern AP to drive the apparatus 200 (including anvil 210, ultrasonic welding device 220 (or adhesive applicator 260), and motor 240) to lay the n elastic strands in each of their respective, predetermined engagement elements 210EL corresponding to the article design profile, including curved elastic sections.

The cam profile actuator 360 is configured to communicate with the anvil pattern profile manager 350 and receive profile parameters such as the shape, location, and dimensions of each point in the article design profile, including each point in the article that is to include an elastic strand, and the shape, location, and dimensions (groove width, seal width, notch axis angle) of each entrapment element 210EL on the anvil face 210F, including the location and dimensions of the ridge line 210RL. Based on the cam profile, the cam profile actuator 360 outputs, or causes the processor 310 to output, control signals to the driver suite 370 to control operation of the motor 240 (and, thereby, the applicator arm 250) via the arm driver 370C by controlling velocity of the motor 240. The cam profile can also be applied to control the anvil driver 370A and horn driver 370B to control the velocity of the anvil 210 and application of energy by the ultrasonic welding device 220 in synchronization with, and matched to, the article design profile.

The cam profile actuator 360 calculates the kingpin effect based on the lag distance LD and generates a kingpin effect correction. The cam profile actuator 360 updates the cam profile for the anvil face 210 to generate a corrected cam profile that includes the kingpin effect correction. The cam profile actuator 360 applies the corrected cam profile and, via the arm driver 370C, moves the actuator arm 250 to position and lay the n elastic strands 12 in predetermined, respective entrapment elements 210EL according to the corrected cam profile, such that the bonded material 21 at the output of the apparatus 200 contains the n elastic strands in the exact same locations as in the article design profile, including each curved section that is to include an elastic strand.

In the driver suite 370: the anvil driver 370A is configured to output voltage and amperage control signals to the motor (not shown) connected to the anvil 210, for example, via a rotary shaft (shown in FIG. 6), and control the rotational velocity of the motor; the horn driver 370B is configured to output voltage, current, and pressure control signals to the ultrasonic welding device 220 to control energy output and the pressure applied by the horn 220H to the anvil face 210F.

FIG. 14 illustrates an example of an article of manufacture 400 that is made by die cutting a section of the bonded material 21, folding the section in half, and attaching the ends to each other to form the article. In this example, the article is an adult diaper. Since the n elastic strands 12 were entrapped in the nonwoven fabrics 11, 13 in a tensioned state, when the tension is removed the entrapped strands contract in the section of the bonded material 21 to form curved portions, which in the example of the article 400 depicted in the drawing are curved in shape and size to contour a human leg.

Referring to FIGS. 4 and 13, the cam profile actuator 360 is configured to create the cam profile based on the shape and dimensions of die cut pattern for the article of manufacture, including all sections having curved elastic strands, and adjust the cam profile based on the kingpin effect corrections to create a corrected cam profile. During operation of the apparatus 200, the corrected cam profile is used by the controller 300 to drive applicator arm 250, via the motor 240, to lay down the n elastic strands 12 on to the material layer 13 supported by the anvil face 210F of the rotating anvil 210 using an oscillating motion that creates a curved profile. As the anvil 210 rotates, the second material layer 11 is lay on top of the fixedly held elastic strings 12 and material layer 13. The n elastic strands 12 are not captured in between the layers 11, 13 until the two layers 11, 13 are bonded together by the ultrasonic welding device 220. The lag distance LD—that is, the distance between where the n elastic strands are applied by the application end 250-1 of the arm 250 and where they are bonded by the horn 220H—is matched by the corrected cam profile so that the applicator arm 250, as it oscillates to-and-fro along a width of the anvil face 210F, lays down each of the n elastic strands in its respective engagement element 210EL in the ridge line 210RL on the anvil face 210F. The corrected cam profile is created to control the oscillating applicator arm 250 such that none of the n elastic reaches an extreme of the anvil face 210F profile. The corrected cam profile is created to correct for the lag distance LD by steering wide the strand application end 250-1 (shown in FIGS. 3-4) such that at all times each of the n elastic strands fall on the anvil face 210F where intended at the bond point between the layers 11, 13.

Figure 15:
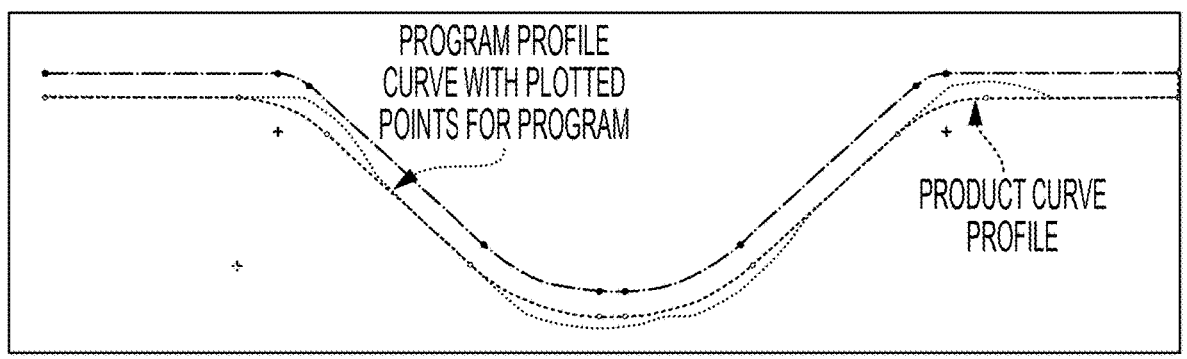
FIG. 15 illustrates an example of an operation of an applicator arm according to an cam profile.

FIG. 15 illustrates an example of an operation of the applicator arm 250 according to the corrected cam profile. As seen in the drawing, where the article profile curve is running in a straight line the kingpin effect will be an extension of that line equal to the lag distance LD. Where there are curves in the article profile curve the kingpin effect will be a line that runs tangent to a point on the curve and extends out the lag distance LD.

Figure 16:
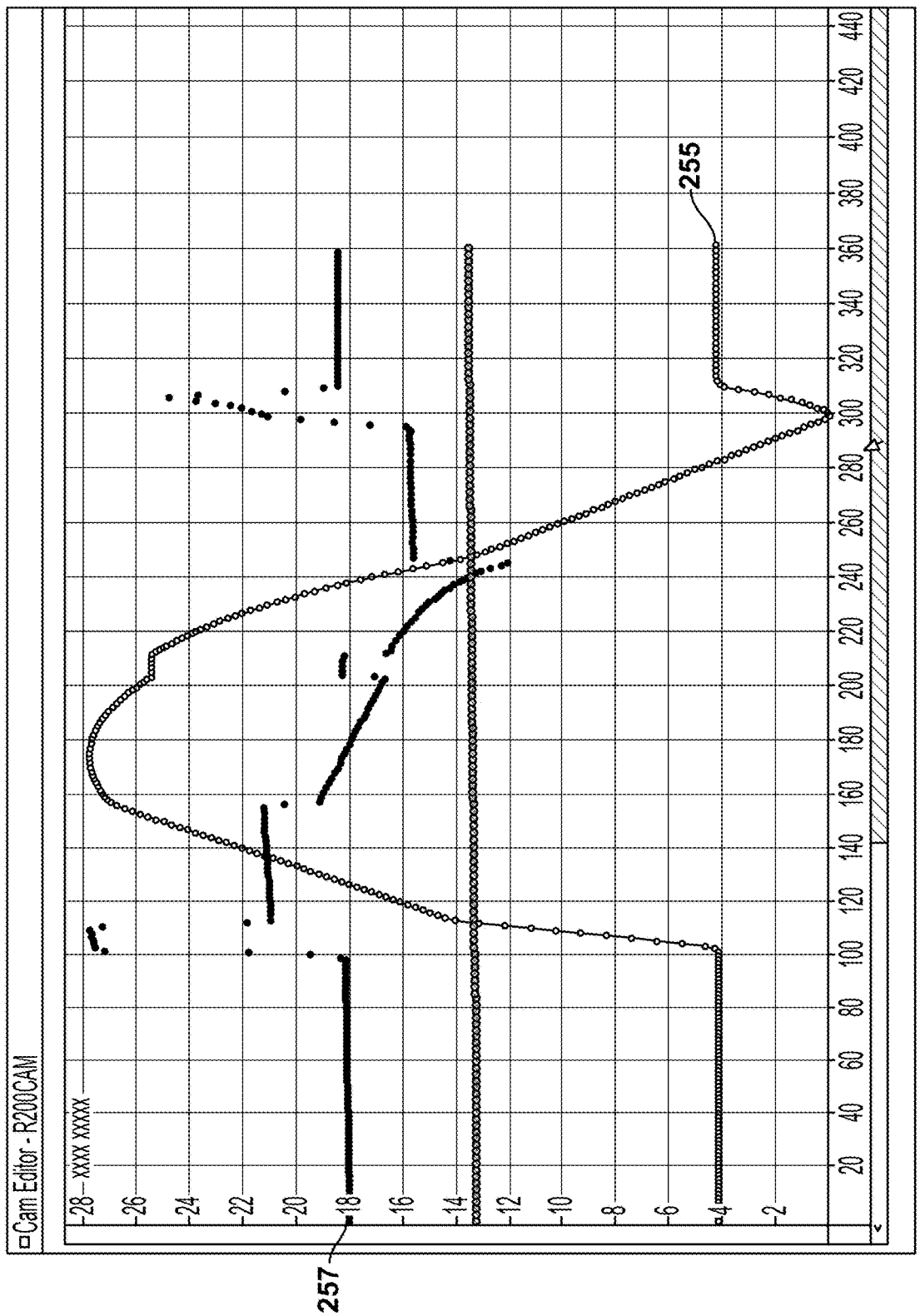
FIG. 16 illustrates a velocity-acceleration diagram for an operation of an applicator arm according to a cam profile.

FIG. 16 illustrates a velocity-acceleration diagram for an operation of an applicator arm according to the corrected cam profile. The sine-like wave pattern is the speed-versuslocation of the arm 250 relative to the anvil face 210F, and the other wave patterns correspond to the acceleration/deceleration values of the arm 250, operating according to the corrected cam profile. As seen in the diagram, the applicator end 250-1 of the arm 250 swings to the left or the right of, and beyond, an entrapment element 210EL, to position and lay a strand 12 in the entrapment element 210EL.

Figure 17:
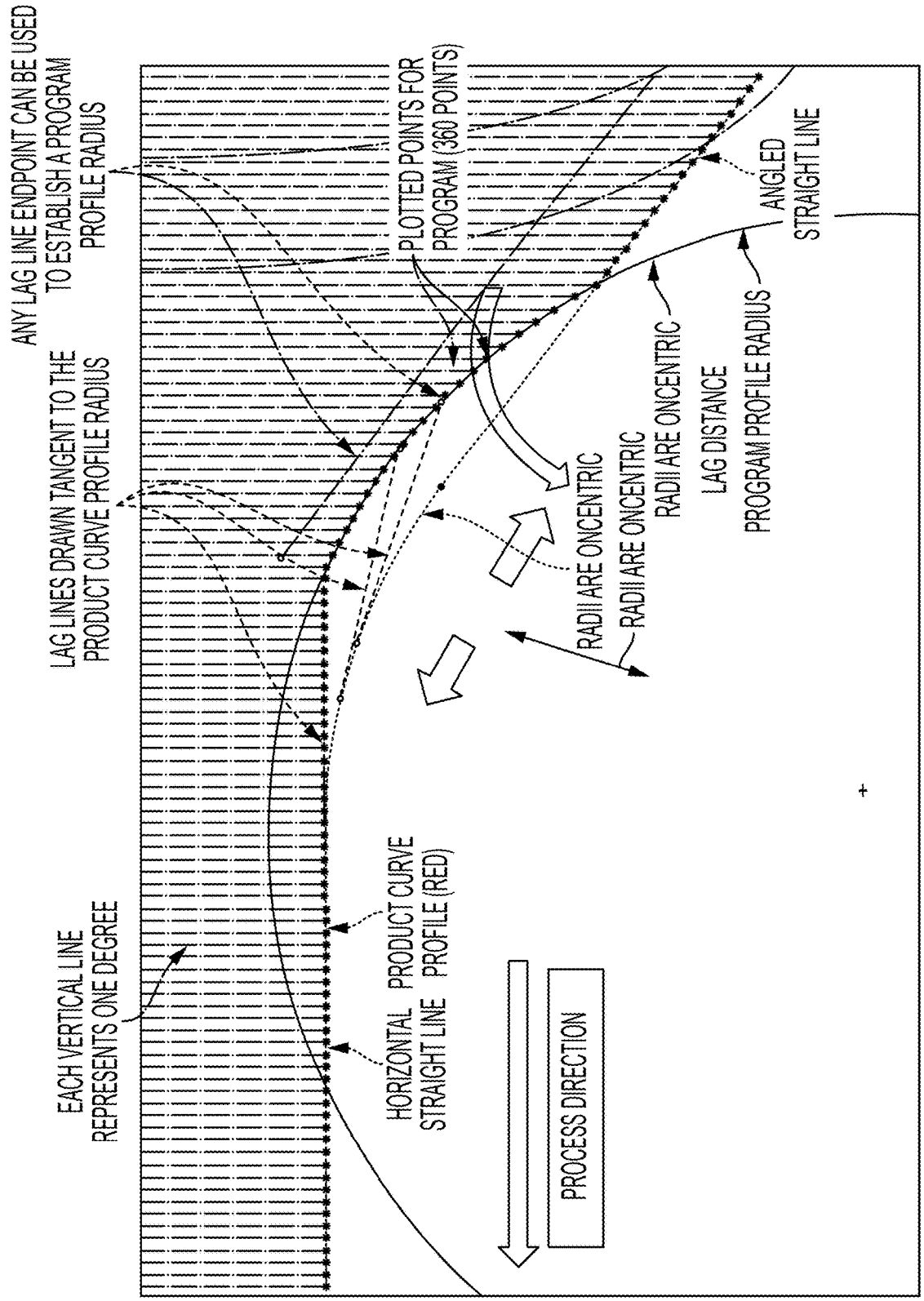
FIG. 17 illustrates another example of an operation of the application arm.

FIG. 17 illustrates another example of an operation of the application arm 250. Referring to the drawing, to create a program profile radius, the cam profile actuator 360 (shown in FIG. 13) can start with the radius concentric to the product profile radius. The radius arc is to be coincident with the outboard endpoint of any lag line. The lag lines can be calculated at any angle but must be tangent to the product profile radius. The lag lines are used to establish a program profile radius.

As seen in FIG. 16, points can be calculated at the intersection of the program profile curve and each vertical line that represents one degree around the anvil roll 210. In the illustration, above the calculated points follow the horizontal line until that line intersects the radius created by the extended lag lines. The points follow that radius until that radius intersects the angled straight line. This process is followed for all transitions on the product profile. The x-y coordinates of these points are used to build or update the program profile.

Figure 18:
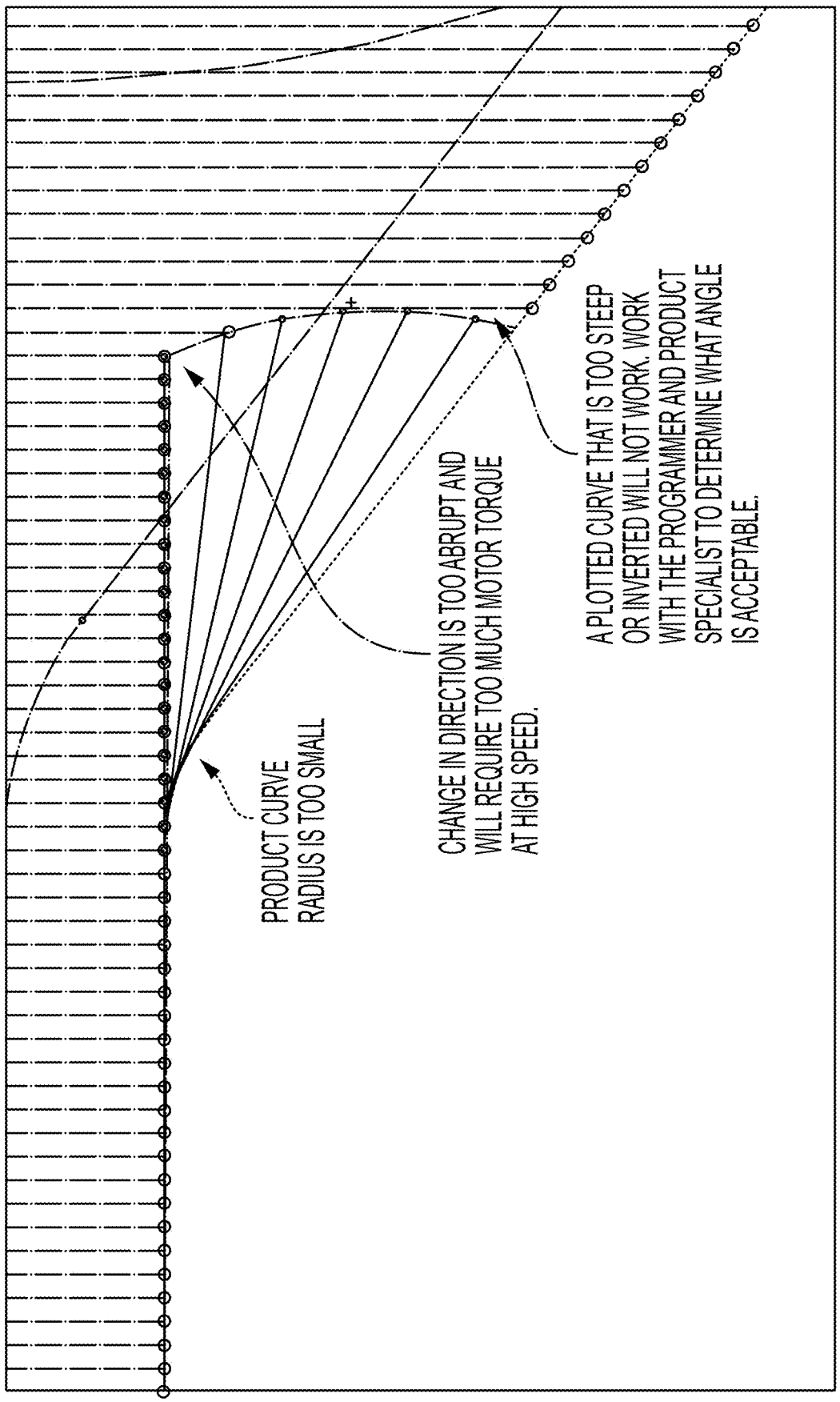
FIG. 18 illustrates an example of a program profile with varying radii.

FIG. 18 illustrates an example of a program profile with varying radii. As seen, radii of a product profile that are too small result in points that change too abruptly, are too steep or inverted, resulting in a program profile that requires too much motor torque or a program that defies physics. The program profile can be created or updated to adjust radii and curves so that the calculated points do not have harsh transitions and steep angles. Radii may be added at these transitions to produce a softer program profile. This will cause the profile to deviate from the product specification. Accordingly, the program profile is configured to avoid radii that are too small and to correct for any deviations from the product specification.

Figure 19:
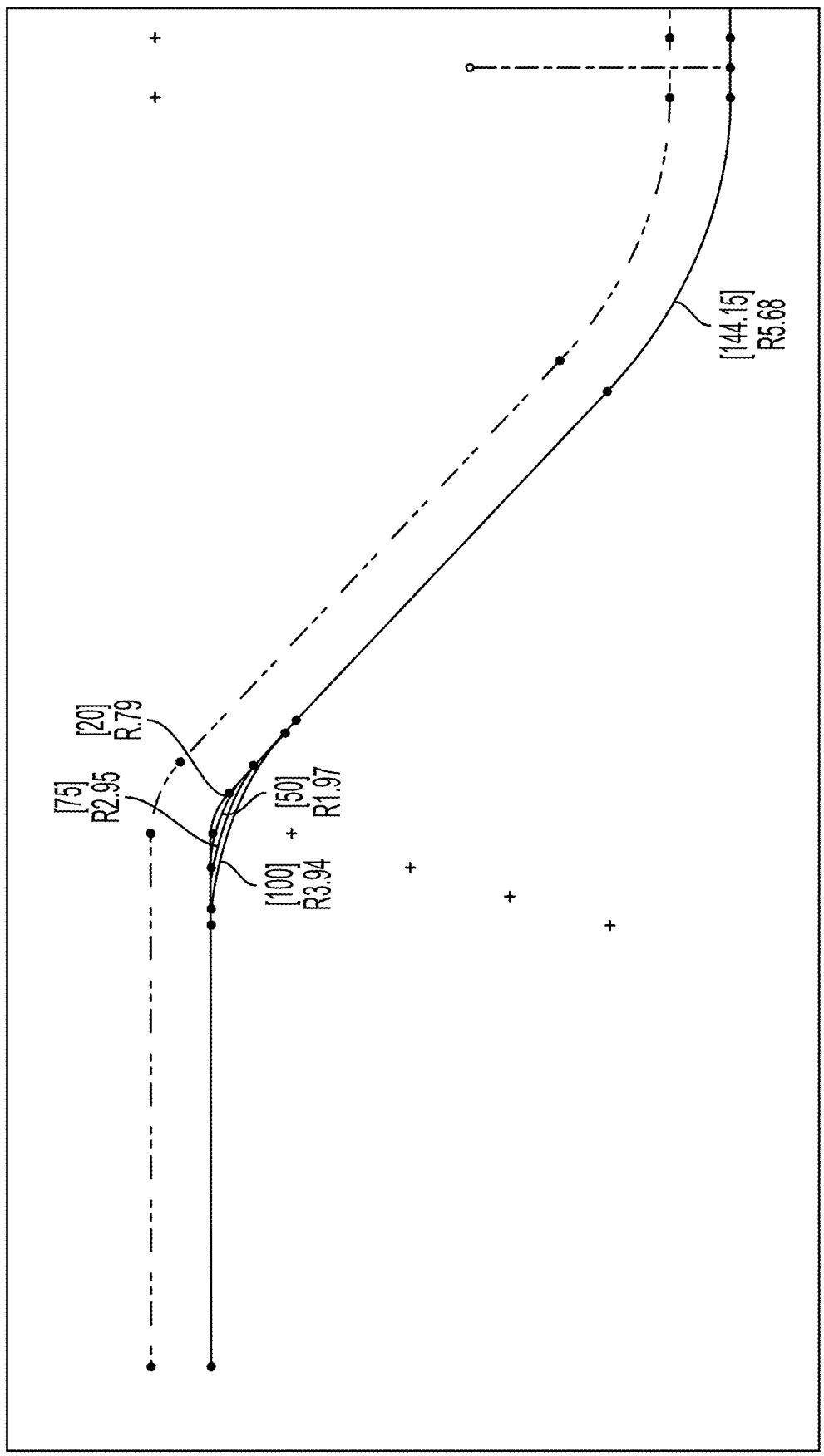
FIG. 19 illustrates examples of how changes to a first and last radii affect a program profile curve.

FIG. 19 illustrates examples of how changes to the first and last radii affect the program profile curve. The initial curve has a radii 20 mm (R20 mm) to show how the larger radii change the overall curve, and the other curves include radii 50 mm (R50 mm), 75 mm (R75 mm), and 100 mm (R100 mm), as seen in FIGS. 20-23.

Figure 20:
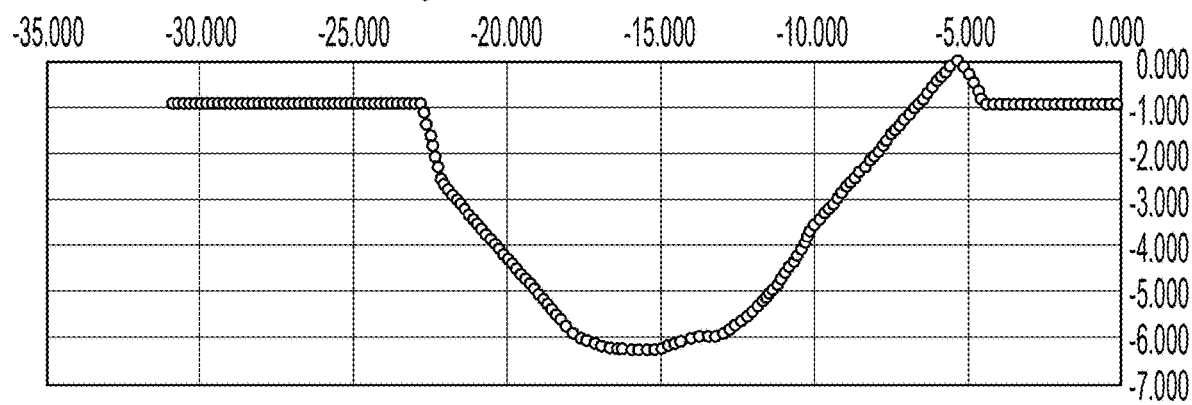
FIG. 20 illustrates an example of an R20 mm curve for curved elastic anvil coordinates 46-46-46-46

FIG. 20 illustrates an example of an R20 mm curve for curved elastic anvil coordinates 46-46-46-46. The curve includes actual points with no softening of sharp corners.

Figure 21:
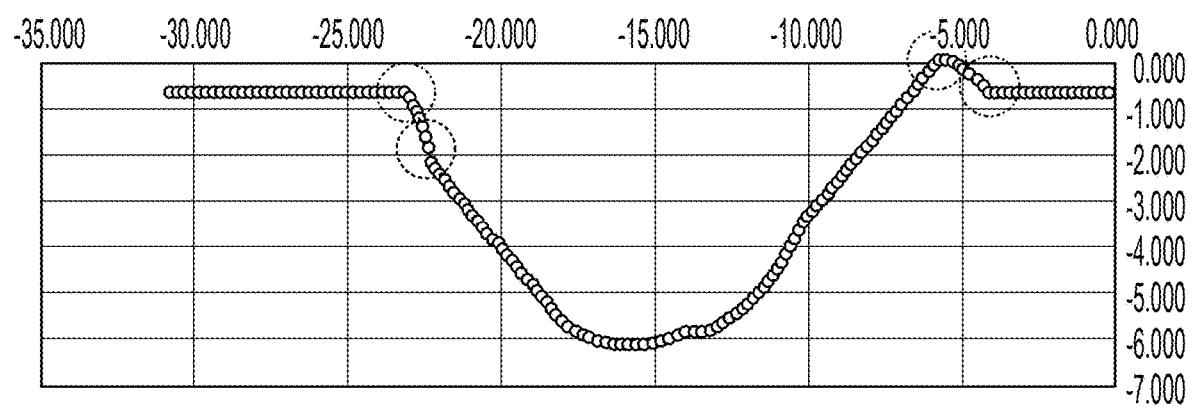
FIG. 21 illustrates an example of an R50 mm curve for curved elastic anvil coordinates 46-46-46-46.

FIG. 21 illustrates an example of an R50 mm curve for curved elastic anvil coordinates 46-46-46-46. The large spacing between points in the red oval indicate a very steep angle. A large radius could be added to transition into the angled slope. A small radius can be added to the yellow areas to reduce motor torque requirements.

Figure 22:
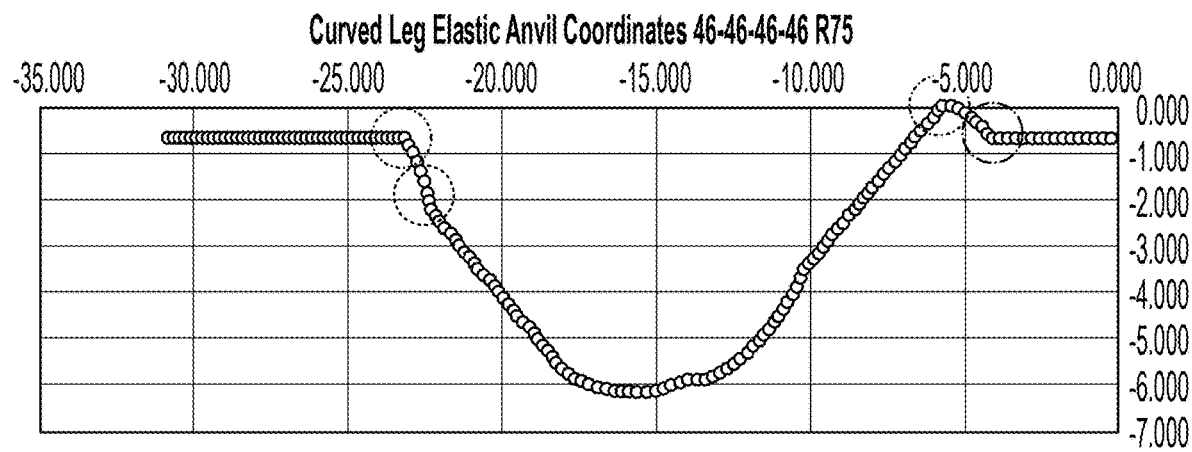
FIG. 22 illustrates an example of an R75 mm curve for curved elastic anvil coordinates 46-46-46-46.

FIG. 22 illustrates an example of an R75 mm curve for curved elastic anvil coordinates 46-46-46-46. In this example, a small radius can be added to the yellow areas to reduce motor torque requirements.

Figure 23:
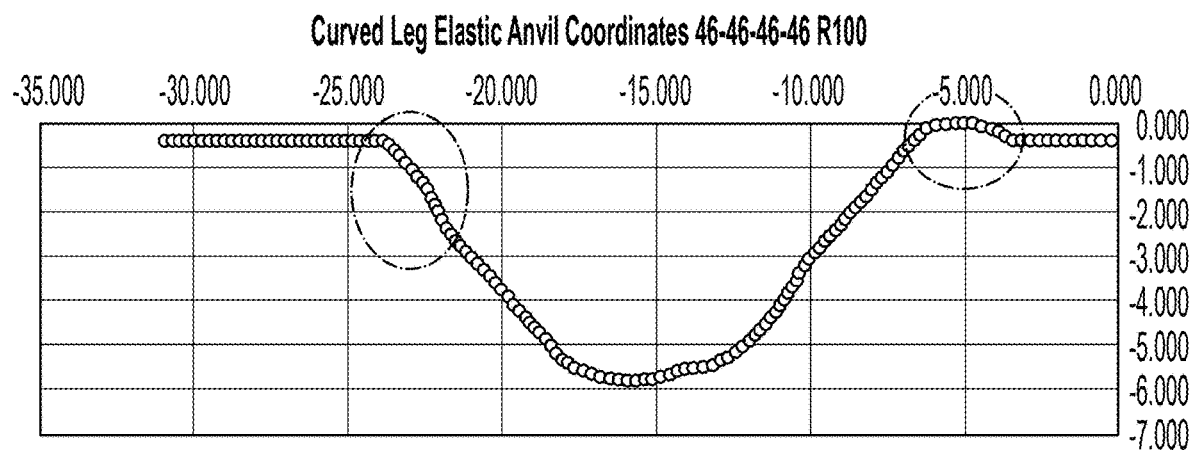
FIG. 23 illustrates an example of an R100 m curve for curved elastic anvil coordinates 46-46-46-46.

FIG. 23 illustrates an example of an R100 m curve for curved elastic anvil coordinates 46-46-46-46. As seen in the drawing, all transitions and slopes are low risk and can easily be implemented by the applicator arm 250 to accurately align and lay the n strands in predetermined entrapment elements on the anvil face 210F.

Devices that are in communication with each other need not be in continuous communication with each other unless expressly specified otherwise. In addition, devices that are in communication with each other may communicate directly or indirectly through one or more intermediaries.

Although process steps, method steps, or algorithms may be described in a sequential or a parallel order, such processes, methods and algorithms may be configured to work in alternate orders. In other words, any sequence or order of steps that may be described in a sequential order does not necessarily indicate a requirement that the steps be performed in that order; some steps may be performed simultaneously. Similarly, if a sequence or order of steps is described in a parallel (or simultaneous) order, such steps can be performed in a sequential order. The steps of the processes, methods or algorithms described in this specification may be performed in any order practical.

When a single device or article is described, it will be readily apparent that more than one device or article may be used in place of a single device or article. Similarly, where more than one device or article is described, it will be readily apparent that a single device or article may be used in place of the more than one device or article. The functionality or the features of a device may be alternatively embodied by one or more other devices which are not explicitly described as having such functionality or features.

What is claimed is:

1. An apparatus for fabricating an elasticized material having at least one elastic strand transversely positioned across the apparatus and along an elastic strand velocity vector direction, the apparatus comprising:
   a first bonding module; and
   a second bonding module positionable in proximity to the first bonding module,
   wherein at least one of the first bonding module and the second bonding module has a face with a width dimension and a circumferential axis and is rotatable about an axis, the face having a repeating contour pattern containing a plurality of ridges,
   wherein the plurality of ridges contain at least a first ridge and a second ridge adjacent to the first ridge, the first ridge and the second ridge each comprising lands and notches constructed to receive and hold the at least one elastic strand,
   wherein the first ridge comprises a notch aligned with a corresponding notch in the second ridge such that said notch and said corresponding notch are arranged to accept the at least one elastic strand, and
   wherein said notch and said corresponding notch each have a different longitudinal axis that is between −30° and +30° from the at least one elastic strand velocity vector direction.

2. The apparatus in claim 1, wherein:
   the other of said at least one of the first bonding module and the second bonding module includes a welding device; and
   each of said plurality of ridges has a ridge line that is perpendicular to said elastic strand velocity vector direction.

3. The apparatus in claim 1, wherein each of the lands has a land width and each of the notches has a notch width, and wherein each of the individual ridges has a land-to-notch ratio of 60:40, or less.

4. The apparatus in claim 1, wherein the land width is between 0.005 inches and 0.013 inches.

5. The apparatus in claim 1, wherein the notches have a depth that is between 0.004 inches and 0.015 inches.

6. The apparatus in claim 1, wherein the notch width is between 0.005 inches and 0.013 inches.

7. The apparatus in claim 1, wherein the at least one elastic strand is between 300 and 1100 decitex.

8. The apparatus in claim 1, wherein the lands have a length that is between 0.015 inches and 0.060 inches.

9. The apparatus in claim 1, wherein the notches have a length that is between 0.015 inches and 0.060 inches.

10. The apparatus in claim 1, wherein the ridges within the repeating contour pattern have a machine direction spacing of 0.10 inches, or greater.

11. The apparatus in claim 1, further comprising:
a strand applicator,
wherein the strand applicator is configured to transversely position the at least one elastic strand in a notch on the individual ridges within the repeating contour pattern.

12. The apparatus in claim 11, further comprising:
an applicator,
wherein the applicator has a strand application end arranged to position and lay the at least one elastic strand in a notch on the individual ridges within the repeating contour pattern, and
wherein the said strand application end is located 150 mm, or less, from the contact line between the first bonding module and second bonding module.

13. The apparatus in claim 11, further comprising:
an applicator having a strand application end located at a lag distance from the contact line between the first bonding module and second bonding module and configured to position and lay at least one elastic strand in one of the plurality of notches in alignment with the repeating contour pattern,
wherein the applicator moves the at least one elastic strand according to a profile which includes kingpin effect corrections created by the lag distance.

14. The apparatus in claim 13, wherein a cam profile having the kingpin effect corrections is configured to move the at least one elastic strand transversely across a width of the second bonding module in alignment with the strand applicator end to-and-fro across the width dimension according to individual notches of each ridge within the repeating contour pattern.

15. The apparatus in claim 13, wherein a minimum radius of a curved section in the repeating contour pattern is a fraction of a king pin lag distance.

16. The apparatus in claim 15, wherein the minimum radius of the curved section at any point in the repeating contour pattern is 30% less than the king pin lag distance.

17. The apparatus in claim 1, wherein the at least one elastic strand is between 300 and 1,100 decitex.

18. A system for fabricating an elasticized material having at least one elastic strand transversely positioned across the apparatus, the system comprising:
a supply station; and
a processing station that includes a first bonding module and a second bonding module positionable in proximity to the first bonding module,
wherein at least one of the first bonding module and the second bonding module has a face with a width dimension and a circumferential axis and is rotatable about an axis, the face having a repeating contour pattern containing a plurality of ridges,
wherein the plurality of ridges contain at least a first ridge and a second ridge adjacent to the first ridge, the first ridge and the second ridge each comprising a plurality of entrapment elements containing notches constructed to receive and hold the at least one elastic strand along an elastic strand velocity vector direction,
wherein the first ridge includes a notch aligned with a corresponding notch in the second ridge such that said notch and said corresponding notch are arranged to accept the at least one elastic strand, and
wherein said notch and said corresponding notch each have a different longitudinal axis that is between −30° and +30° from the elastic strand velocity vector direction.

19. The system in claim 18, further comprising:
an applicator arm having a strand application end located at a lag distance from another of said at least one of the first bonding module and the second bonding;
a driver configured to drive the applicator arm according to a cam profile to position and lay each of the plurality of elastic strands in the plurality of entrapment elements in alignment with curved shape of the ridge,
wherein the cam profile includes kingpin effect corrections to correct for a kingpin effect created by the lag distance.

20. A method for fabricating an elasticized material having a curved elastic section containing the at least one elastic strand, the method comprising:
positioning a first bonding module in proximity to a second bonding module, wherein:
at least one of the first bonding module and the second bonding module has a face with a width dimension and a circumferential axis and is rotatable about an axis, the face having a repeating contour pattern containing a plurality of ridges,
wherein the plurality of ridges contain at least a first ridge and a second ridge adjacent the first ridge, the first ridge and the second ridge each comprising lands and notches constructed to receive and hold the at least one elastic strand along an elastic strand velocity vector direction,
wherein the first ridge comprises a notch aligned with a corresponding notch in the second ridge such that said notch and said corresponding notch are arranged to accept the at least one elastic strand, and
wherein said notch and said corresponding notch each have a different longitudinal axis that is between −30° and +30° from the elastic strand velocity vector direction.

* * * * *